United States Patent
Weber et al.

(10) Patent No.: US 11,433,241 B2
(45) Date of Patent: Sep. 6, 2022

(54) MONITORING AND REGULATING PHYSIOLOGICAL STATES AND FUNCTIONS VIA SENSORY NEURAL INPUTS TO THE SPINAL CORD

(71) Applicant: University of Pittsburgh—Of the Commonwealth System of Higher Education, Pittsburgh, PA (US)

(72) Inventors: Douglas Weber, Pittsburgh, PA (US); Robert Gaunt, Pittsburgh, PA (US); Timothy Bruns, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 796 days.

(21) Appl. No.: 15/462,487

(22) Filed: Mar. 17, 2017

(65) Prior Publication Data
US 2017/0189684 A1 Jul. 6, 2017

Related U.S. Application Data

(62) Division of application No. 13/843,023, filed on Mar. 15, 2013, now Pat. No. 9,622,671.
(Continued)

(51) Int. Cl.
*A61N 1/36* (2006.01)
*A61M 5/172* (2006.01)
(Continued)

(52) U.S. Cl.
CPC ........ *A61N 1/36139* (2013.01); *A61B 5/1107* (2013.01); *A61B 5/202* (2013.01); *A61B 5/24* (2021.01); *A61B 5/4064* (2013.01); *A61B 5/4255* (2013.01); *A61B 5/4393* (2013.01); *A61B 5/4519* (2013.01); *A61B 5/4824* (2013.01); *A61B 5/4836* (2013.01); *A61B 5/7246* (2013.01); *A61M 5/1723* (2013.01);
(Continued)

(58) Field of Classification Search
USPC .......................................................... 607/40
See application file for complete search history.

(56) References Cited

U.S. PATENT DOCUMENTS

| | | | |
|---|---|---|---|
| 5,411,540 A * | 5/1995 | Edell | A61N 1/0543 607/116 |
| 6,862,479 B1 * | 3/2005 | Whitehurst | A61N 1/32 604/503 |

(Continued)

OTHER PUBLICATIONS

Ackermann et al., "Conduction block of peripheral nerve using high-frequency alternating currents delivered through an intrafascicular electrode." *Muscle & Nerve* 41.1: pp. 117-119 (2010).
(Continued)

*Primary Examiner* — Carl H Layno
*Assistant Examiner* — Michael J Lau
(74) *Attorney, Agent, or Firm* — Klarquist Sparkman, LLP

(57) ABSTRACT

Methods and apparatuses for monitoring and regulating physiological states and functions are disclosed. Several embodiments include application of one or more microelectrode arrays to a dorsal root ganglion for measurement of sensory neuron activity, or stimulation of sensory reflex circuits. The methods and apparatuses can be used, for example, for monitoring or controlling bladder function in a patient.

16 Claims, 20 Drawing Sheets

Related U.S. Application Data

(60) Provisional application No. 61/613,314, filed on Mar. 20, 2012.

(51) Int. Cl.

| | |
|---|---|
| *A61B 5/00* | (2006.01) |
| *A61N 1/05* | (2006.01) |
| *A61B 5/24* | (2021.01) |
| *A61B 5/11* | (2006.01) |
| *A61B 5/20* | (2006.01) |
| *A61N 1/02* | (2006.01) |

(52) U.S. Cl.
CPC ........... *A61N 1/025* (2013.01); *A61N 1/0551* (2013.01); *A61N 1/36003* (2013.01); *A61N 1/36007* (2013.01); *A61N 1/36062* (2017.08); *A61N 1/36071* (2013.01); *A61N 1/36082* (2013.01); *A61N 1/36107* (2013.01); *A61B 5/112* (2013.01); *A61B 5/205* (2013.01); *A61B 2560/0223* (2013.01); *A61B 2562/028* (2013.01); *A61B 2562/04* (2013.01)

(56) References Cited

U.S. PATENT DOCUMENTS

| | | | | |
|---|---|---|---|---|
| 6,907,293 | B2* | 6/2005 | Grill | A61N 1/0556 607/2 |
| 7,047,078 | B2* | 5/2006 | Boggs, II | A61N 1/36007 607/2 |
| 7,276,057 | B2 | 10/2007 | Gerber | |
| 7,328,068 | B2 | 2/2008 | Spinelli et al. | |
| 7,328,069 | B2 | 2/2008 | Gerber | |
| 7,337,005 | B2 | 2/2008 | Kim et al. | |
| 7,369,894 | B2 | 5/2008 | Gerber | |
| 7,450,993 | B2 | 11/2008 | Kim et al. | |
| 7,502,651 | B2 | 3/2009 | Kim et al. | |
| 7,565,198 | B2 | 7/2009 | Bennett et al. | |
| 7,571,000 | B2 | 8/2009 | Boggs et al. | |
| 7,580,753 | B2 | 8/2009 | Kim et al. | |
| 7,623,925 | B2 | 11/2009 | Grill et al. | |
| 8,229,565 | B2 | 7/2012 | Kim et al. | |
| 2004/0111126 | A1* | 6/2004 | Tanagho | A61N 1/36071 607/40 |
| 2005/0203588 | A1* | 9/2005 | King | A61N 1/36071 607/48 |
| 2005/0245987 | A1* | 11/2005 | Woods | A61N 1/36185 607/46 |
| 2006/0052826 | A1* | 3/2006 | Kim | A61M 25/06 607/2 |
| 2006/0095088 | A1* | 5/2006 | De Ridder | A61N 1/36085 607/48 |
| 2006/0161236 | A1* | 7/2006 | King | A61N 1/0553 607/117 |
| 2008/0109048 | A1* | 5/2008 | Moffitt | A61N 1/36071 607/46 |
| 2008/0234791 | A1* | 9/2008 | Arle | A61B 5/0031 607/117 |
| 2009/0254144 | A1* | 10/2009 | Bhadra | A61N 1/36007 607/41 |
| 2010/0041972 | A1* | 2/2010 | Mason | A61B 5/296 600/372 |
| 2010/0137938 | A1 | 6/2010 | Kishawi et al. | |
| 2010/0331925 | A1* | 12/2010 | Peterson | A61N 1/36071 607/72 |
| 2011/0021943 | A1* | 1/2011 | Lacour | A61N 1/0551 600/546 |

OTHER PUBLICATIONS

Bahns et al., "Responses of sacral visceral afferents from the lower urinary tract, colon and anus to mechanical stimulation." *Pflügers Archiv*, 410.3: pp. 296-303 (1987).

Bauman et al., "Online feedback control of functional electrical stimulation using dorsal root ganglia recordings." *Engineering in Medicine and Biology Society, EMBC, 2011 Annual International Conference of the IEEE*: pp. 7246-7249 (2011).

Betz et al., "Description of sensory preservation in children and adolescents with incomplete spinal cord injury." *The Journal of Spinal Cord Medicine*, 34.3: pp. 297-300 (2011).

Bošnjak et al. "Motor response of the leg muscles produced by position-selective stimulation of spinal nerve roots." *Neurosurgery*, 47.1: pp. 97-106 (2000).

Bruns et al., "Estimating bladder pressure from sacral dorsal root ganglia recordings." *Engineering in Medicine and Biology Society, EMBC, 2011 Annual International Conference of the IEEE*: pp. 4239-4242 (2011).

Bruns et al., "Multielectrode array recordings of bladder and perineal primary afferent activity from the sacral dorsal root ganglia." *Journal of Neural Engineering* 8.5: p. 056010 (2011).

Bruns et al., "Real-time control of hind limb functional electrical stimulation using feedback from dorsal root ganglia recordings." *Journal of Neural Engineering*, 10.2: p. 026020 (2013).

Bruns et al., "Sacral dorsal root ganglia recordings of bladder and perineal sensory activity", *Society for Neuroscience 41st Annual Meeting, Washington, D.C.*, Nov. 12-16, 2011 (Abstract).

Deer et al., "A prospective study of dorsal root ganglion stimulation for relief of chronic pain." *Neuromodulation*, 16.1: pp. 67-72 (2013).

Gaunt et al., "Microstimulation of primary afferent neurons in the L7 dorsal root ganglia using multielectrode arrays in anesthetized cats: thresholds and recruitment properties." *Journal of Neural Engineering* 6.5: p. 055009 (2009).

Gustafson et al., "A urethral afferent mediated excitatory bladder reflex exists in humans." *Neuroscience Letters* 360.1: pp. 9-12 (2004).

Häbler et al., "Myelinated primary afferents of the sacral spinal cord responding to slow filling and distension of the cat urinary bladder." *The Journal of Physiology*, 463.1: pp. 449-460 (1993).

Iggo, "Tension receptors in the stomach and the urinary bladder." *The Journal of Physiology*, 128.3: pp. 593-607 (1955).

Kirshblum et al., "Predicting neurologic recovery in traumatic cervical spinal cord injury." *Archives of Physical Medicine and Rehabilitation*, 79.11: pp. 1456-1466 (1998).

Ko et al. "Intrathecal movement and tension of the lumbosacral roots induced by straight-leg raising." *American Journal of Physical Medicine & Rehabilitation*, 85.3: pp. 222-227 (2006).

Koopmeiners et al., "Effect of electrical field stimulation on dorsal root ganglion neural function." *Neuromodulation*, 16.4: pp. 304-311 (2013).

Kumar et al., "Epidural spinal cord stimulation for treatment of chronic pain—some predictors of success. A 15-year experience." *Surgical Neurology*, 50.2: pp. 110-121 (1998).

Majerus et al., "Low-power wireless micromanometer system for acute and chronic bladder-pressure monitoring." *Biomedical Engineering, IEEE Transactions on*, 58.3: pp. 763-767 (2011).

Melgaard et al., "Detecting the onset of urinary bladder contractions using an implantable pressure sensor." *Neural Systems and Rehabilitation Engineering, IEEE Transactions on* 19.6: pp. 700-708 (2011).

Mendez et al., "Estimation of bladder volume from afferent neural activity." *IEEE Transactions on Neural Systems and Rehabilitation Engineering*, 21.5: pp. 704-715 (2013).

Park et al., "Detecting bladder fullness through the ensemble activity patterns of the spinal cord unit population in a somatovisceral convergence environment." *Journal of Neural Engineering*, 10.5: p. 056009 (2013).

Peckham et al., "Functional Electrical Stimulation for Neuromuscular Applications," *Annu. Rev. Biomed. Eng.*, 7: pp. 327-360 (2005).

Saleh et al., "Detection of the bladder volume from the neural afferent activities in dogs: experimental results." *Neurological Research* 30.1: pp. 28-35 (2008).

Selionov et al., "Tonic central and sensory stimuli facilitate involuntary air-stepping in humans." *Journal of Neurophysiology*, 101.6: pp. 2847-2858 (2009).

(56) References Cited

OTHER PUBLICATIONS

Smith et al., "Development of an implantable networked neuroprosthesis." *Neural Engineering, 2005. Conference Proceedings. 2nd International IEEE EMBS Conference on. IEEE*: pp. 454-457 (2005).
Spinelli et al., "Latest technologic and surgical developments in using InterStim™ therapy for sacral neuromodulation: impact on treatment success and safety." *European Urology* 54.6: pp. 1287-1296 (2008).
Tai et al., "Bladder inhibition or voiding induced by pudendal nerve stimulation in chronic spinal cord injured cats." *Neurourology and Urodynamics* 26.4: pp. 570-577 (2007).
Weber et al., "Decoding sensory feedback from firing rates of afferent ensembles recorded in cat dorsal root ganglia in normal locomotion." *Neural Systems and Rehabilitation Engineering, IEEE Transactions on*, 14.2: pp. 240-243 (2006).
Weber et al., "Limb-state feedback from ensembles of simultaneously recorded dorsal root ganglion neurons." *Journal of Neural Engineering*, 4.3: pp. S168-S180 (2007).

\* cited by examiner

Example raw data showing evoked hindlimb force vectors

Magnitude and direction of evoked forces indicated by length and orientation of lines.

MONITORING AND REGULATING PHYSIOLOGICAL STATES AND FUNCTIONS VIA SENSORY NEURAL INPUTS TO THE SPINAL CORD

RELATED APPLICATIONS

This application is a divisional of U.S. application Ser. No. 13/843,023, filed Mar. 15, 2013, now U.S. Pat. No. 9,622,671; which in turn claims the benefit of U.S. Provisional Application No. 61/613,314, filed Mar. 20, 2012; each of these applications is specifically incorporated by reference herein in its entirety.

ACKNOWLEDGMENT OF GOVERNMENT SUPPORT

This invention was made with government support under Grant Nos. EB007749 and NS056136 awarded by the National Institutes of Health and Grant No. W81XWH-07-1-0716 from the Telemedicine and Advanced Technology Research Center. The government has certain rights in the invention.

FIELD

The present disclosure relates to the field of physiological monitoring and stimulation and specifically to the electrophysiological monitoring and stimulation of sensory inputs to the spinal cord at one or more dorsal root ganglia.

BACKGROUND

The spinal cord provides sensory and motor innervation to the neck, torso, and limbs. Sensory information from the skin, muscles, joints, and some internal organs is relayed to the spinal cord by sensory neurons whose cell bodies are located in the dorsal root ganglia (DRG) that lie immediately adjacent to the spinal cord. That sensory information is routed to neural networks in the spinal cord and brain, contributing directly to the formation of conscious sensory experiences (i.e., perception) and to the regulation of motor and autonomic functions. In contrast, the ventral nerve roots that emanate from the spinal cord convey efferent information to the periphery. While information from these sensory neurons would be very useful for patients with various neurological disorders, there are no practical technologies for continuous long-term monitoring of such sensory signals.

Functional electrical stimulation (FES) of efferent pathways provides a mechanism for the direct control of musculoskeletal, respiratory, bladder, rectal, and sexual function after brain and spinal cord injury. Further, electrical stimulation of afferent pathways can be used to provide a mechanism for the control of muscle, bladder, rectal, and sexual function after brain and spinal cord injury, by leading to reflex activation of spinal circuits and recruitment of efferent pathways. However, current FES applications operate mainly in an open-loop mode, without automatic regulation or biological input to modulate the stimulation, and continuous feedback control has yet to be fully implemented in most FES applications due to multiple challenges. Further, current methods for activating afferents activate an entire nerve or nearby nerves and thus other undesired functions, are likely to occur.

SUMMARY

Methods and apparatuses for monitoring and regulating physiological states and functions are disclosed. The disclosed methods include contacting at least one dorsal root ganglion in the patient with a microarray. For example the methods can include contacting the dorsal root ganglion with a penetrating microarray, or closely coupling a microarray to the surface of a dorsal root ganglion, in the patient. Several embodiments include application of one or more microelectrode arrays to a DRG for measurement of sensory neuron activity, or stimulation of sensory reflex circuits. The methods and apparatuses can be used, for example, for monitoring or controlling bladder function in a patient.

In some embodiments, methods of monitoring a physiological state of an organ or a tissue in a patient are disclosed. Such methods include a calibration phase and a monitoring phase. The calibration phase includes measuring sensory neuron activity with the individual electrodes, and correlating the sensory neuron activity with the physiologic state of the organ or the tissue in the patient to identify individual electrodes in the array that measure the sensory neuron activity associated with the physiological state. The monitoring phase includes measuring the sensory neuron activity associated with the physiological state with the identified individual electrodes, and outputting an indication of the physiological state of the organ or the tissue to, for example, an effector (such as a device or system for use in FES therapy), or to user interface, a computer readable storage medium, or a local or remote computer system. In some examples, the user interface alerts the patient to the measurement of the physiological state. In further embodiments, the effector is an electronic stimulator or other device (such as a drug pump) that regulates the function of the tissue or organ.

In some embodiments, methods of inducing a physiological function of an organ or a tissue in a patient are disclosed. Such methods include a calibration phase and an inducement phase. The calibration phase includes stimulating sensory neuron with the individual electrodes to activate a sensory reflex circuit that induces the physiological function of the organ or the tissue, and correlating activation of the physiological function with the stimulated sensory neuron to identify individual electrodes that can activate the sensory reflex circuit that induces the physiological function. The inducement phase includes activating the sensory reflex circuit by stimulating the sensory neuron with the identified individual electrodes to induce the physiological function in the patient.

Additional embodiments include an apparatus for monitoring or regulating the physiologic state of an organ or a tissue in a patient. The apparatus includes a microelectrode array implanted into or coupled closely to a surface of at least one dorsal root ganglion of the patient, wherein the array comprises a plurality of individual electrodes. The array is operably linked to a circuit for assessing sensory neuron activity measured through the individual electrodes of the array, and a circuit for calculating the physiologic state of the organ from the sensory neuron activity. The apparatus further includes a mechanism for alerting the patient of the physiologic state of the organ or the tissue or for storing the physiologic state for reference, and a mechanism for regulating an effector, such as a neurostimulator, drug pump or other effector using feedback signals from the organ or tissue.

In one embodiment, the disclosed methods and apparatuses are used to monitor the physiological state of a bladder, such as fullness or lack of fullness. In another embodiments, the disclosed methods are used to induce a bladder function, such as voiding or continence.

The foregoing and other objects, features, and advantages of the embodiments will become more apparent from the following detailed description, which proceeds with reference to the accompanying figures.

BRIEF DESCRIPTION OF THE FIGURES

In FIG. 10, the actual hip-to-toe distance of a limb and the spike counts for two DRG units are given at the top. The regression model coefficients were updated every 200 ms, indicated by the vertical dashed lines. Regression coefficients for the two units are shown. Continuous updates to the regression model during calibration phase, based on updates to the coefficients for all DRG units, yield improved estimates of the end point position, at the top, and the RMS error, as shown at bottom.

In FIG. 12A, action potential waveforms from isolated single neurons are shown in the left column, modulated neural activity signals are shown in the middle column (gray) with foot position signals overlaid in black, and inter-spike-interval (ISI) histograms shown in the right column. DRG neural signals recorded in this way can be used to estimate the angular positions of the knee and ankle joints (FIG. 12B). In these plots, the first 45 seconds of data were used to calibrate the regression model, and the accuracy of the model was then tested in the remaining ~60 seconds of data.

DETAILED DESCRIPTION

The DRG presents a unique target for the placement of multi-electrode arrays and possesses several characteristics that have not been previously exploited. Since a single DRG contains afferent fibers from an entire region of the body, a single microelectrode array placed at a DRG can access many specific functions that vary depending on the spinal level of the DRG. Uniquely, DRGs also have little internal organization. Thus, electrode arrays can record and stimulate a wide variety of afferent fibers without having to be specifically designed to target particular DRG sub-compartments. Such an organization would require development of electrodes arrays with specific and targeted geometries, greatly increasing their complexity. A regular grid of electrodes can successfully sample a large portion of the total function imparted through a single DRG. Further, stimulation at very low intensities ($\leq 10$ μA) through just one microelectrode on an array can induce functionally relevant physiologic outcomes, such as bladder contractions that could induce bladder voiding. Combining stimulation through multiple electrodes can result in simultaneous activation of multiple responses.

It is also possible to record DRG neural activity from single cells using non-penetrating electrodes that are closely coupled to the surface of a DRG. This is possible because of the close proximity of neuronal cells to the DRG surface. This is in sharp contrast to recording in other structures like the brain, where neuronal cell bodies may be millimeters below the surface, and peripheral nerves where signals from individual axons cannot be differentiated with a surface electrode. Therefore, a single microelectrode array implanted in, or in close coupling with one structure (the DRG) allows for both the recording and activation of either individual or groups of neurons with functional relevance.

These unique features of the DRG were exploited in the disclosed methods and apparatuses, which are useful, for example to monitor or regulate physiological states and functions in a patient.

Apparatuses

The disclosed methods employ an array of microelectrodes inserted into or closely coupled with one or more DRG that are effective to monitor or stimulate the activity of dozens of sensory neurons, for example, originating from the skeletal muscles, skin, bladder, urethra, and rectum. The particular DRG targeted for microelectrode array implantation or coupling depends on the physiological state or function that the method or apparatus is designed to monitor or regulate. In some instances one or more DRG may be targeted. One of skill in the art will recognize which DRG is appropriate for the particular physiological state or function that the method is designed to monitor or regulate.

Figure 1:
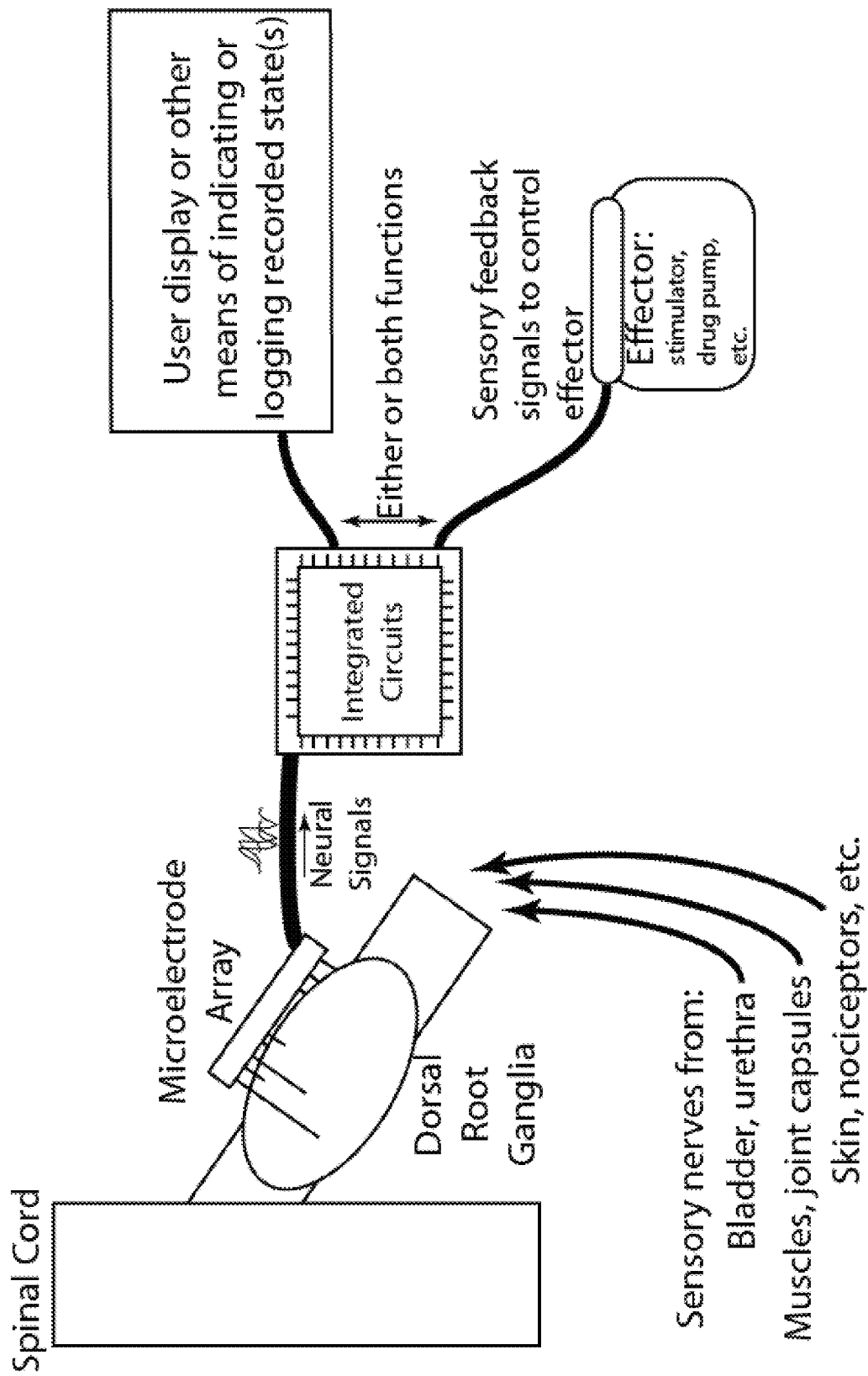
FIG. 1 displays a block diagram of an embodiment of a disclosed apparatus for monitoring DRG neuronal activity.

An exemplary apparatus for use with the disclosed monitoring methods is illustrated in FIG. 1. In this embodiment, a microelectrode array is attached to one or more DRG in which the electrodes either penetrate into the DRG (at the same or different depths) or are closely coupled to the surface of the DRG. Measured neural signals are sent to integrated circuits or external systems which track the physiologic state(s) and either may be used to notify the user (via a user interface through, for example, tactile or visual notification) of a need to respond to a state, or to maintain closed-loop control of a prosthetic device (such as a neuroprosthesis) for maintaining control of a function, such as bladder control.

Figure 4:
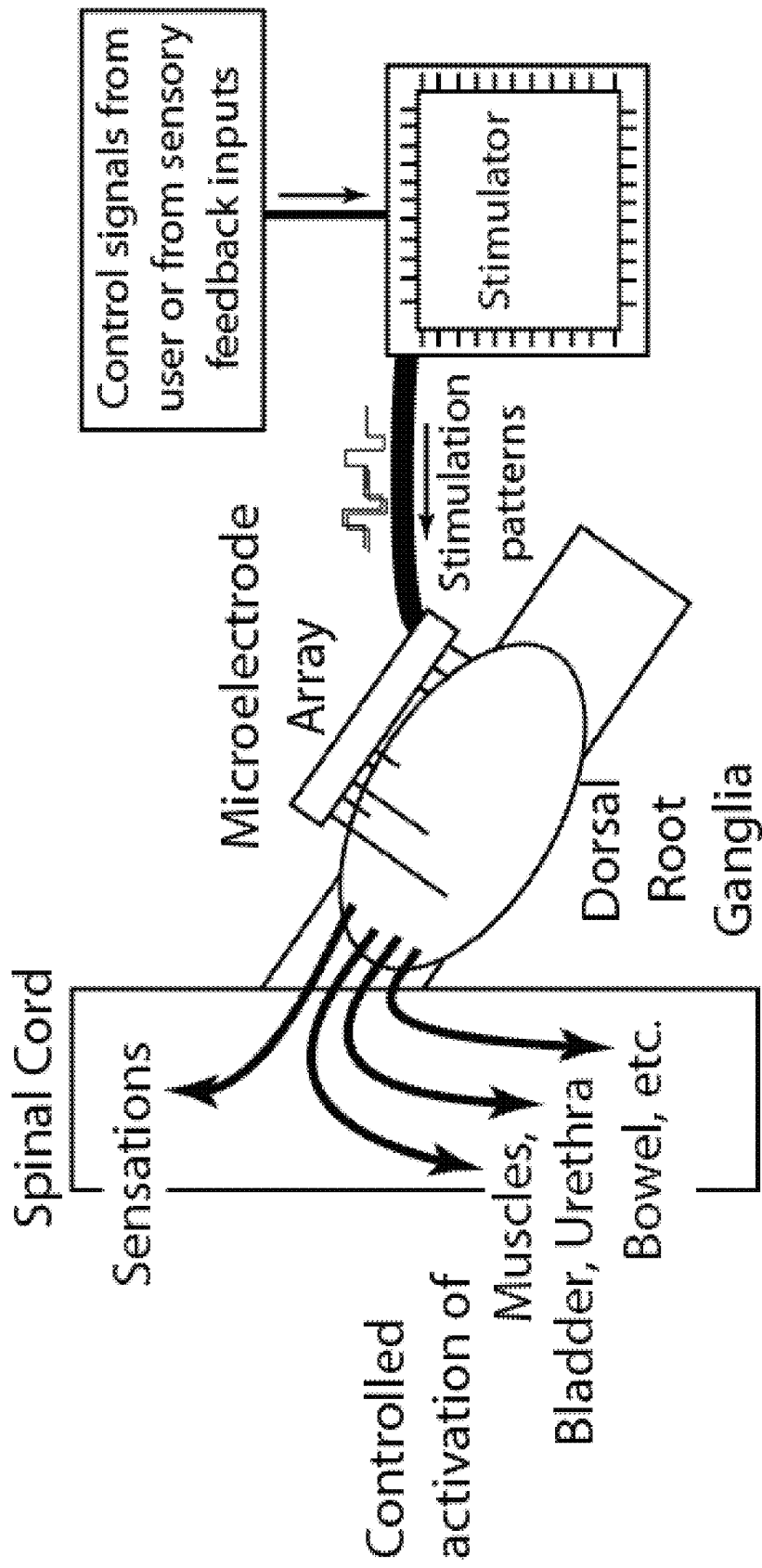
FIG. 4 shows a schematic diagram of an embodiment of a disclosed apparatus utilized to stimulate DRG neurons to achieve functional control of a physiologic process by activating a sensory neuron reflex circuit or to evoke perceptible sensations.

An exemplary apparatus for use with the disclosed stimulating methods is illustrated in FIG. 4. In this embodiment, a microelectrode array is attached to one or more DRG in which the electrodes either penetrate into the DRG (at the same or different depths) or are closely coupled to the surface of the DRG. Each microelectrode in an array may be used to deliver electrical current to the DRG at an intensity that is sufficient to activate one or more sensory neurons in close proximity to the electrode. Varying the electrical current pattern applied to one or more electrodes creates specific stimulation patterns at the level of the DRG, which in turn has a direct influence on the activation of neurons and neuronal circuits in the spinal cord.

The array utilized in the disclosed embodiments may be a penetrating array wherein the electrodes on the array penetrate into the DRG. The electrodes can penetrate to any point within the DRG with a preference for areas having densely packed cell bodies, which typically occurs near the perimeter of the DRG. The electrodes can be the same or different lengths. For example, the electrodes on the array can be of different lengths and penetrate the DRG at different depths. The electrodes are of a suitable length for insertion into the DRG, for example from 100 µm to 3 mm in length. In an alternative embodiment, the array is a non-penetrating array, and the electrodes on the array do not penetrate the DRG, and instead are closely coupled to the surface of the DRG. In embodiments including a closely coupled array, the electrodes are typically incorporated into the base member, the base member optionally being a flexible member that can conform to the surface of the DRG, such that the electrode length is flush with or extends only a short distance from the base member facing the DRG. Non-limiting examples of microelectrode arrays are provided in the Examples, below. The person of ordinary skill in the art will appreciate that the electrodes on any of the penetrating or non-penetrating arrays are suitable for recording and/or stimulating single neurons or groups of neurons within the DRG.

The array includes a plurality of individual electrodes that are capable of detecting and/or stimulating activity from one or more neurons. Electrode size and spacing may be set at a wide range of values as dictated by the specific implementation, condition, and anatomical location of the electrode placement The individual electrodes are designed for measuring and/or stimulating activity from single neurons or small clusters of neurons. Typically the array includes at least 5 electrodes, such as at least 6, 7, 8, 9, 10, 15, 20, 30, 40, 50, 60, 70, 80, 90, or 100 or more electrodes. The pattern of the electrodes on the array can vary depending on the particular application. In several embodiments, the electrodes are spaced equally across the array. Non-limiting examples include arrays with 1×5, 1×6, 1×7, 1×8, 1×9, 1×10, 2×10, 3×10, 4×10, 5×10, or 6×10 arrays of electrodes. The electrodes on the array may have a surface area of less than 200,000 $\mu m^2$, such as less than 150,000 $\mu m^2$, less than 100,000 $\mu m^2$, less than 75,000 $\mu m^2$, less than 50,000 $\mu m^2$, less than 10,000 $\mu m^2$, or less than 5,000 $\mu m^2$. In some embodiments, the electrodes are less than 100 µm in diameter (such less than 75 µm or less than 50 µm in diameter). In additional embodiments, the electrodes can have a diameter of from 30-50 µm in diameter. However, any diameter or surface area that can measure and/or stimulate single neuron activity can be used for the individual electrodes. Although the individual electrodes on the array are suitable for measuring and/or stimulating activity from single neurons, the person of skill in the art will appreciate that measurement and/or stimulation from multiple neurons is also possible.

The electrodes on the array can be designed to penetrate into or for close coupling to the DRG. In some embodiments, the electrodes are of a sufficient length to penetrate deeply into the a DRG (e.g., >200 um). In other embodiments, the electrodes are of a sufficient length to penetrate into the epineurium, but not into the body of a DRG (e.g., <100 um). In further embodiments, the electrodes are of a sufficient length to contact the surface of the ganglia but do not penetrate the epineurium. In some embodiments, the electrode lengths may vary among one, two or all three of these electrode depths or each electrode may have a length that is distinct from all other electrode lengths.

The array can be inserted into, or closely coupled with, any DRG in a patient, depending on the physiological state or function to be monitored or controlled. In several embodiments, the array is inserted into or closely coupled with sacral level DRGs, such as a S1, S2, S3, or S4 DRG. In some embodiments, more than one array is inserted into or closely coupled with DRGs in a patient. For example, a first array can be inserted into or closely coupled with a S1 DRG, and a second array can be inserted into, or closely coupled with a S2 DRG. In another example, first and second arrays are inserted into or closely coupled with bilateral DRG, such as a left and right S1 DRGs.

In some embodiments, the microelectrode array(s) are operably linked to integrated circuitry that track the physiologic state(s) indicated by the neuronal activity measured by the electrodes in the array. The person of ordinary skill in the art is familiar with integrated circuitry for use with microelectrode arrays, and such circuitry is further described herein. The integrated circuits can be fully implanted (typically implantable in a subcutaneous pocket within a patient's body) or partially implanted in the patient, but are not limited thereto. The operable linkage to the array can be by way of one or more leads, although any operable linkage capable of transmitting the measured neuronal activity signal from the electrodes on the array to the integrated circuitry can be used. The circuitry is typically capable of utilizing one or more algorithms (e.g., regression algorithms) to convert the neural activity into an estimate of the current physiological status of the associated organ or system. A variety of algorithms may be used, including those described in the Examples section below, and one of skill in the art will recognize which algorithm is appropriate for the particular sensory input being measured.

As illustrated in FIG. 1, measured neural signals are sent to integrated circuits and/or external systems and further may be used to notify the user (via a user interface through, for example, tactile or visual notification) of a need to respond to a state or to maintain closed-loop control of a neuroprosthetic device for maintaining control of a function, such as bladder control. Thus, in some embodiments, the integrated circuitry is operably linked to a user interface to display information concerning the measured neuronal signals. In some embodiments, an indication of the physiological state is output to an effector, such as a neuroprosthetic or stimulation device for control of an organ (e.g., bladder), reanimation of a paralyzed muscle, or control of a movement disorder. The integrated circuitry is typically configured for outputting an indication of the physiological state to the user interface, the effector, or both.

In some embodiments, the integrated circuitry includes a stimulator operably linked to the array and suitably designed for application of various current, voltage, pulse rate, waveforms etc., for generating neuronal activity in one or more neurons in proximity to the individual electrodes in the array. For example, the stimulator can be separate from the integrated circuitry or it can be included in the same housing as the integrated circuitry.

Thus, in several embodiments, the integrated circuitry can be used to monitor or to generate and provide electrical stimulation (via one or more of the microelectrodes on the array) to neurons in the DRG. The integrated circuitry can comprise and/or be included within a controller (e.g., processor) for controlling the operations of the device, including stimulating, signal transmission, charging and/or using energy from a battery for powering the various components of the circuitry, and the like. Typically, the integrated circuitry includes a pulse generator that provides stimulation energy in programmable patterns adapted for direct stimulation of sensory neurons within a DRG. Additional details regarding neuron stimulation, monitoring, and electrical circuitry for use therefore are known to the person of ordinary skill in the art, see for example, U.S. Pat. Nos. 7,502,651 and 7,450,993, which are incorporated herein by reference.

In several embodiments, the microelectrode array, integrated circuitry, stimulator, and/or other features of an apparatus for use with a disclosed method can be fully implanted (typically implantable in a subcutaneous pocket within a patient's body) or partially implanted in the patient. Further, the microelectrode array, integrated circuitry, stimulator, and/or other features of an apparatus for use with a disclosed method can be attached to nearby spinal vertebrae to stabilize the apparatus, thus securing the apparatus during normal motion and activities by the patient. The features of the apparatus for use with the disclosed methods are typically made of materials that are suitable for medical use and implantation into a human patient. Therefore, in several embodiments, the apparatus is provided in sterile form for use in a patient.

While the aspects of the disclosed apparatus involving physiological monitoring of DRG neurons and the stimulation of inherent reflexes or afferent pathways are described separately above, they may be integrated into a single apparatus to be employed to achieve the goals articulated herein. For example, the same microelectrode array inserted into a DRG may be utilized to both measure sensory afferent activity as well as reflexively activate efferent pathways through sensory afferent stimulation. The circuitry employed to achieve these goals may be integrated into a single housing to provide for a single device useful for patients and the medical practitioners treating them.

Methods of Monitoring and Stimulating

Methods are provided for monitoring one or more physiological states in a patient via sensory neural inputs to the spinal cord. The monitoring can be used, for example, to monitor the fullness (or lack thereof) of the bladder, tremor or rigidity associated with Parkinson's disease or other movement disorders, pressure ulcers, pain and/or limb position. The monitoring can also be used to provide sensory feedback information concerning a physiological state to support a closed loop treatment. Also provided are methods of regulating one or more physiological functions in a patient including stimulation of sensory reflex circuits to induce or promote the function.

The disclosed methods include contacting (such as implanting or closely coupling) a microelectrode array to a DRG in the patient. The selected DRG typically is one that is known to receive sensory neuron input concerning the physiological state or function to be monitored or regulated. The array includes a plurality of individual electrodes configured for measuring and/or stimulating activity of one or more sensory neurons in the DRG.

The methods provided for monitoring a physiological state typically include a calibration phase and a monitoring phase. The calibration phase includes measuring a threshold amount of sensory neuron activity (e.g. an amount of activity above a noise level). The sensory neuron activity measured by the individual electrodes in the array is correlated with the physiologic state in the patient to identify individual electrodes in the array that measure the sensory neuron activity associated with the physiological state.

Once individual electrodes that measure the activity of neurons associated with the physiological state are identified, the activity of these neurons can then be monitored to infer the physiological state. Thus, the monitoring phase includes measuring the sensory neuron activity associated with the physiological state with the identified individual electrodes. When detected, an indication of the physiological state can be outputted, for example, to an effector (such as a device or system for use in neuroprosthesis therapy, or electrical microstimulator), or to a user interface, a computer readable storage medium, or a local or remote computer system. In several embodiments, the effector is under user control.

The apparatus used in monitoring methods includes circuitry that measures and processes neural activity generated by sensory neurons in close proximity to each electrode in the array. Algorithms are used to convert the neural activity into an estimate of the current physiological status of the associated organ or system. A variety of algorithms may be used, including those described in the Examples section below, and one of skill in the art will recognize which algorithm is appropriate for the particular sensory input being measured. Physiologic states or signals that may be estimated include bladder pressure (e.g., bladder fullness and lack of fullness), urethral flow (such as desired or undesired urine flow), urethral sphincter closure, bladder contractions or relaxation, fullness of the colon and rectum, anal sphincter closure, and painful sensations (such as harmful tissue compression) from the skin or other organs including deep tissue where pressure sores may originate. Additionally, muscle force, position and motion, and other proprioceptive states or signals may be assessed, including respiratory rate for detecting apnea. Once the identity of the neuron or neurons being recorded is determined, the activity of that neuron(s) may be used to selectively measure specific physiologic variables associated with the activity of that neuron.

In some embodiments, output from the sensory measurements may be used to control a display or trigger an alert (e.g., notify insensate patients of unsafe stimuli/pressure applied to the skin that may result in a pressure ulcer) or may be logged externally, for example with a computer readable storage medium, or a local or remote computer system. In further embodiments, output from the sensory measurements may be used to control as inputs to a neuroprosthetic or stimulation device for control of an organ (e.g., bladder), reanimation of a paralyzed muscle, or control of a movement disorder.

The methods provided for inducing a physiological function also typically include a calibration phase and an inducement phase. The calibration phase includes determining a level of stimulation that must be applied with the individual electrodes in the microelectrode array to stimulate sensory neuron activity and activate a sensory reflex circuit that induces the physiological function (e.g., bladder continence or voiding). The level of stimulation is correlated with inducement of the physiological function to identify individual electrodes that can activate the sensory reflex circuit that induces the physiological function.

Once individual electrodes that can be stimulated to activate a sensory neuron reflex circuit inducing a particular physiological response (e.g., bladder continence) are identified, the activity of these neurons can then be stimulated to induce the physiological state. Thus, the inducement phase includes stimulation of the identified individual electrodes that activate the sensory neuron reflex circuit that induces the physiological function.

Targeted stimulation of more than one DRG sensory neuron cell or groups of cells by more than one microelectrode may lead to coordinated events including, for example, bladder voiding (bladder excitation and urethral sphincter relaxation), bladder continence (bladder relaxation and urethral sphincter excitation) as well as fecal continence, emptying of the colon and rectum, sexual arousal, ejaculation, and multi-joint limb movements. Targeted stimulation may also activate sensory pathways to the brain that lead to tactile or proprioceptive sensations (for example in persons with prosthetic limbs or impaired peripheral sensory function including diabetes) or may mask or block painful sensations or generate paresthesias in the patient. The methods and apparatuses allow for the microstimulation of many individual cells or groups of cells at multiple distinct locations in one or more DRG to achieve that variety of effects. The methods and apparatuses are able to achieve these physiological results through the coordinated and selective activation of multiple independent and/or synergistic pathways without activation of unwanted pathways that would occur using stimulation using larger electrodes that activate larger portions of a DRG.

Thus, the methods can be used to achieve activation of physiologic reflexes and sensory pathways through direct microstimulation of DRG neurons. The methods thus can be used by individuals who do not respond to medications and other conservative treatments for bladder incontinence, voiding dysfunction, or other pelvic disorders, who are unable to move their limbs, who are experiencing painful sensations, or who are lacking adequate sensory percepts. The methods also can provide a mechanism by which stimulation across multiple microelectrode channels may be employed to restore normal bladder function, to enhance other physiological responses, to provide relief from pain or to counter muscle fatigue. As described in the Examples below, the methods are effective for achieving bladder relaxation or contraction. This finding is further reflective of the utility of the methods for impacting numerous physiological systems to restore levels of relatively normal functioning in diverse anatomical systems whose function is mediated by spinal sensory reflex circuitry at all levels of the spinal cord.

The methods may be employed in a variety of contexts, including to monitor the tremor, rigidity, and bradykinesia in patients with Parkinson's disease and other movement disorders (e.g., spasticity, dystonia). The methods may also be employed for tremor detection and closed-loop control of deep brain stimulation (DBS). Similarly, the methods may be employed in the monitoring of respiratory functions allowing detection of apnea and subsequently trigger an alarm or effector for restoring breathing.

One of skill in the art will recognize that the methods may be implemented employing a wide variety of components and for a diversity of other physiologic conditions. For example, the methods may be employed to monitor body positioning and activation of appropriate muscles in spinal injury patients.

In some embodiments, the methods are used to monitor or regulate bladder or bowel function. In such embodiments, DRG receiving sensory input from the bladder or bowel are targeted for contact with the microelectrode (e.g., array implantation or coupling). Sacral DRG S1-S4 are known to contain sensory neurons receiving signals from the bladder and bowel (see, e.g., Vodusek, *Digestion*, vol. 69, no. 2, pp. 87-92, 2004, which is incorporated by reference in its entirety). Thus, in some embodiments, the sacral DRG S1-S4 are targeted for measurement of sensory neuron activity that correlates with bladder pressure or distension, urethral flow, and for bowel pressure or distension. Measurement of sensory neuron activity correlated with the physiological state of the bladder or bowel (e.g., pressure, such as fullness, or lack of fullness) can be outputted to a user interface, a computer readable storage medium, or a local or remote computer system, or an effector. Sacral DRG S1-S4 can also be targeted for stimulation of sensory reflex circuits to induce or promote bladder or bowel function (e.g., continence or clearance).

In some embodiments, the methods are used to monitor the physiological state of, or stimulate, sexual organs. In such embodiments, DRG receiving sensory input from the sexual organs (e.g., penis or vagina) are targeted for contact with the microelectrode (e.g., array implantation or coupling). Sacral DRG S2-S4 are known to contain sensory neurons receiving signals from the sexual organs (see, e.g., Vodusek, *Digestion*, vol. 69, no. 2, pp. 87-92, 2004, which is incorporated by reference in its entirety). Thus, in some embodiments, sacral DRG S2-S4 are targeted for measurement of sensory neuron activity correlated with arousal or erection. Measurement of sensory neuron activity correlated with arousal or erection can be outputted to a user interface, a computer readable storage medium, or a local or remote computer system, or an effector (e.g., in a closed loop embodiment). Sacral DRG S2-S4 can also be targeted for stimulation of sensory reflex circuits to induce or promote sexual organ function (e.g., arousal, erection, ejaculation).

In some embodiments, the methods are used to monitor or prevent the presence of a pressure sore. In such embodiments, DRG receiving sensory input from tissue susceptible to a pressure sore (e.g., tissue near a bony protrusion, such as the ischial tuberosity or heels) are targeted for contact with the microelectrode (e.g., array implantation or coupling). Lumbar DRG L4, L5, and/or sacral DRG S1 are known to contain sensory neurons receiving signals from tissue susceptible to a pressure sore (see, e.g., Betz et al., *J Spinal Cord Med*, 34(3):297-300, 2011, which is incorporated by reference in its entirety). Thus, in some embodiments, lumbar DRG L4, L5, and/or sacral DRG S1 are targeted for measurement of sensory neuron activity correlated with the presence of a pressure sore, such as activity in pain and/or pressure receptors to detect harmful tissue compression and/or the onset of a pressure sore. Measurement of sensory neuron activity correlated with the presence of a pressure sore can be outputted to a user interface, a computer readable storage medium, or a local or remote computer system, or an effector. In some embodiments, the effector is a functional electronic stimulator that stimulates muscle activity to promote pressure relief or to increase blood flow to the tissue susceptible to the pressure sore. Lumbar DRG L4 and L5, and sacral DRG S1 can also be targeted for stimulation of sensory reflex circuits to evoke reflexive muscle activity to improve blood flow in tissue susceptible to a pressure sore.

In some embodiments, the methods are used to monitor or prevent the symptoms of a movement disorder (e.g. spasticity, bradykinesia, rigidity, tremor), such as Parkinson's disease. In such embodiments, DRG receiving sensory input from upper or lower limbs are typically targeted for contact with the microelectrode (e.g., array implantation or coupling). Lumbar DRG L2, L3, L4, L5, and/or sacral DRG S1 are known to contain sensory neurons receiving signals from the lower extremities affected by movement disorders (see, e.g., Bosnjak et al., *Neurosurgery*, 47(1):97-105, 2000; Ko et al., *Am J Phys Med Rehabil*, 85(3):222-7, 2006; Kirshblum et al., *Arch Phys Med Rehabil*, 79(11):1456-66, 1998, each of which is incorporated by reference in its entirety). Further, cervical DRG C3, C4, C5, C6, C7, thoracic DRG T1 are known to contain sensory neurons receiving signals from the upper extremities affected by movement disorders (see, e.g., Kirshblum et al., *Arch Phys Med Rehabil*, 79(11):1456-66, 1998, which is incorporated by reference in its entirety). Thus, in some embodiments, cervical DRG C3, C4, C5, C6, C7, thoracic DRG T1, lumbar DRG L2, L3, L4, L5, and/or sacral DRG S1 are targeted for measurement of sensory neuron activity correlated with symptoms of movement disorders including spasticity, bradykinesia, rigidity, and tremor. Measurement of sensory neuron activity correlated with the movement disorder can be outputted to a user interface, a computer readable storage medium, or a local or remote computer system, or an effector. In some embodiments, the effector is a brain stimulator, such as a deep brain stimulator implanted to treat Parkinsonian tremor, which is activated in response to the outputted signal.

In some embodiments, the methods are used as a sensory augmentation in patients with sensory neuropathy. For example, stimulation at the DRG can aid or augment cutaneous sensations in foot and joint motion to improve balance control in the patient. Lumbar DRG L2, L3, L4, L5, and/or sacral DRG S1 are known to contain sensory neurons receiving signals from the lower extremities and that can activate sensory reflex circuits to the lower extremities (see, e.g., Bosnjak et al., *Neurosurgery*, 47(1):97-105, 2000; Ko et al., *Am J Phys Med Rehabil*, 85(3):222-7, 2006; Kirshblum et al., *Arch Phys Med Rehabil*, 79(11):1456-66, 1998, each of which is incorporated by reference in its entirety). Thus, in some embodiments, lumbar DRG L2, L3, L4, L5, and/or sacral DRG S1 are targeted for stimulation as a sensory aid/augmentation for patients with sensory neuropathy to improve balance control.

In some embodiments, the methods are used to activate or inhibit leg muscle function for standing and walking. Lumbar DRG L2, L3, L4, L5, and/or sacral DRG S1 are known to contain sensory neurons that can activate sensory reflex circuits to the lower extremities including the muscles required for standing and walking (see, e.g., Bosnjak et al., *Neurosurgery*, 47(1):97-105, 2000; Ko et al., *Am J Phys Med Rehabil*, 85(3):222-7, 2006; Kirshblum et al., *Arch Phys Med Rehabil*, 79(11):1456-66, 1998, each of which is incorporated by reference in its entirety). Thus, in some embodiments, lumbar DRG L2, L3, L4, L5, and/or sacral DRG S1 are targeted for stimulation of sensory reflex circuits for the activation or inhibition of leg muscle synergies for standing and walking. The methods may be used in combination with other forms of electrical stimulation to control leg muscle function in the patient. It will be understood that, in closed loop-embodiments, the disclosed methods of monitoring sensory neuronal activity can be used to detect sensory signals correlated with leg movement status, and outputted to a stimulator.

In some embodiments, the methods are used to monitor sensory afferents in the DRG associated with walking or limb movement and are used in combination with electrical stimulation of nerve fibers to correct foot drop or other gait deficits in patients. Lumbar DRG L2, L3, L4, L5, and/or sacral DRG S1 are known to contain sensory neurons that monitor the state of the lower limb (see, e.g., Bosnjak et al., *Neurosurgery*, 47(1):97-105, 2000; Ko et al., *Am J Phys Med Rehabil*, 85(3):222-7, 2006; Kirshblum et al., *Arch Phys Med Rehabil*, 79(11):1456-66, 1998, each of which is incorporated by reference in its entirety) and that when stimulated can activate sensory reflex circuits to the lower extremities that correct foot drop or other gait deficits. Thus, in some embodiments, lumbar DRG L2, L3, L4, L5, and/or sacral DRG S1 are targeted for stimulation of sensory reflex circuits that correct foot drop. The methods may be used in combination with other forms of electrical stimulation to control foot drop in the patient. It will be understood that, in closed loop-embodiments, the disclosed methods of monitoring sensory neuronal activity can be used to detect sensory signals correlated with foot drop status, and outputted to the stimulator.

In some embodiments, the methods are used to monitor sensory afferents in the DRG associated with sensory reflex circuits controlling hand grasp motion, and are used in combination with electrical stimulation of nerve fibers to improve or restore hand grasp motion in patients. In such embodiments, DRG receiving sensory input from upper limbs are targeted for microelectrode array implantation or coupling. Cervical DRG C5, C6, C7 and/or thoracic DRG T1 are known to contain sensory neurons that that monitor the state of hand grasp motion (see, e.g., Kirshblum et al., *Arch Phys Med Rehabil*, 79(11):1456-66, 1998, which is incorporated by reference in its entirety)) and that when stimulated can activate sensory reflex circuits to the upper extremities that can improve or restore hand grasp motion in patients. Thus, in some embodiments, cervical DRG C5, C6, C7 and/or thoracic DRG T1 are targeted for stimulation of sensory reflex circuits that induce or promote hand grasp motion. The methods may be used in combination with electrical stimulation of nerves controlling hand grasp or arm motion in the patient. It will be understood that, in closed loop-embodiments, the disclosed methods of monitoring sensory neuronal activity can be used to detect sensory signals correlated with hand grasp motion status, and outputted to the stimulator.

In some embodiments, the methods are used to monitor breathing rate and lung distension and to also stimulate sensory reflex circuits to pace the diaphragm and/or elicit cough. In such embodiments, DRG receiving sensory input, or capable of activating sensory reflex circuits, from respiratory tissue can be targeted for microelectrode array implantation or coupling. Cervical DRG C3, C4, C5 and/or thoracic DRG T4-T11 are known to contain sensory neurons receiving input from tissue involved with breathing rate and distension, and that can activate sensory reflex circuits that induce diaphragm function or elicit cough. Thus, in some embodiments, cervical DRG C3, C4, C5 and/or thoracic DRG T4-T11 are targeted for measurement of sensory neuron activity correlated with breathing rate or lung distension. Measurement of sensory neuron activity correlated with the presence of a breathing rate or lung distension can be outputted to a user interface, a computer readable storage medium, or a local or remote computer system, or an effector. Further, in some embodiments, DRG C3, C4, C5 and/or thoracic DRG T4-T11 are targeted for stimulation of sensory reflex circuits to pace the diaphragm and/or elicit cough.

While the aspects of the disclosed methods involving physiological monitoring of DRG neurons and the stimulation of inherent reflexes or afferent pathways are described separately above, they may be integrated into a single apparatus and method. For example, the same microelectrode array inserted into a DRG may be utilized to both measure sensory afferent activity as well as reflexively activate efferent pathways through sensory afferent stimulation. In such methods, the circuitry employed in the apparatus may be integrated into a single housing to provide for a single device useful for patients and the medical practitioners treating them. As a specific embodiment, the method may be used to monitor and regulate the bladder using circuitry specifically tailored for monitoring and stimulating S1-S4 DRG neuronal activity. The patient may then be alerted to the status of the bladder (e.g., fullness or lack thereof). Stimulation circuitry may be employed to maintain bladder continence until the patient is ready to empty their bladder. Related stimulation circuitry may then be employed to cause an appropriate emptying of the bladder. The methods may be employed similarly to achieve appropriate emptying of the bowel/colon. The methods may also be employed in a similar manner to achieve sexual arousal and performance in impotent patients or patients with spinal injuries.

Description of Certain Aspects of Neuronal Modulation

Pelvic and pudendal nerves carry sensory signals to the lumbosacral spinal cord conveying information about the state of the bladder, urethra, and perineal region. Sensory neurons in the bladder wall provide the neural signals that convey information about bladder volume and/or pressure, thus providing individuals with a sense of bladder fullness and facilitate emptying of the bladder. Similarly, sensory neurons embedded in muscles and tendons measure the length, rate of stretch, and contraction force of muscles. Other groups of sensory neurons transmit sensations of irritation and pain to the spinal cord. Additionally, information from pudendal nerve afferents supports sexual activity and arousal. Efferent portions of the pelvic, pudendal, and other sacral nerves innervate the bladder and the urethral and anal sphincters and are involved with voiding the bladder, emptying the rectum, orgasm and sexual arousal.

While information from these sensory neurons would be very useful for patients having compromised spinal circuitry, there are no practical technologies for continuous long-term monitoring of bladder pressure or other sensory signals. For example, several non-invasive devices using ultrasound technology can estimate the bladder pressure or volume; however, they are typically used only in the clinic and are not appropriate for mobile, functioning individuals. Temporary catheterization allows for bladder monitoring, but this is a procedure performed in the clinic and can have undesirable side effects, as well as cause discomfort and lead to infections. Implanted bladder pressure sensors are under pre-clinical development (e.g., Majerus et al., 2011 IEEE TBME, 58: 763-7 and Melgaard and Rijkhoff, 2011 IEEE TNSRE, 19:700-8, which are hereby incorporated by reference) however they have yet to show long-term viability, do not take advantage of natural sensory integration by the body's neural circuitry and are only targeted for a single organ. Recordings from peripheral nerves to detect bladder contractions (e.g., Saleh et al., 2008, Neurolog Res, 30: 28-35, which is hereby incorporated by reference) are also under pre-clinical development, though these approaches must compensate for small signals and interference from non-bladder neural signals and only target a single organ. Moreover, such methods rely on monitoring a proxy of the bladder contraction itself and cannot monitor bladder pressure in the absence of a contraction. Due to the fine structure of the innervation of the bladder, direct monitoring of peripheral nerve signals to the bladder is currently not possible. Other non-neural interface approaches, such as electrical impedance plethysmography remain in preclinical research due to challenging obstacles.

These sensory nerve signals may provide valuable information to patients. For example, sensory input from sacral afferent nerves may provide spinal compromised patients with valuable information regarding the physiological state of the bowels, bladder, and sexual organs. Spinal cord injured patients may not be able to assess those physiological states and as a result can suffer from episodes of potentially life threatening autonomic dysreflexia, as well as incontinence, impotence, and general discomfort. Additionally, many individuals with neurological disorders such as stroke or spinal injury are unable to respond to changes in their bladder or rectum and are also susceptible to pressure sores. Physiologic monitoring of processes leading to pressure sore formation is particularly important for such patients. Pressure sores tend to initiate internally close to bony prominences and by the time they are visible externally, are already well developed. In insensate patients, such as those with spinal cord injury, methods to monitor the body's natural sensors could reduce the risk of developing pressure sores. Furthermore, patients with movement disorders such as dystonia and Parkinson's disease experience symptoms such as rigidity, tremor, and spasticity that are often difficult to quantify. Sensory nerve signals from muscle afferent neurons can provide a direct and continuous measure of muscle tone and joint motion for evaluating the status of the neuromuscular system in patients with movement disorders. Thus, measurement of the activity of those neuronal inputs may allow compromised patients greater information about their physiological state and, thus, when coupled with the appropriate ability to control motor outputs, greater control over those important physiological functions.

Several studies have tested direct interfaces with the nervous system and have demonstrated an ability to detect bladder contractions from pelvic nerve, pudendal nerve, and sacral root whole-nerve recordings. However, these approaches must compensate for small signals recorded from the whole nerve and interference from non-bladder signals before they are able to be employed effectively. Similarly, single-unit activity from individual pelvic, pudendal, and sacral root afferent fibers has been recorded in cats and shows a high correlation to bladder pressure as well as urethra, colon, and rectal activities (e.g., Bahns et al., 1987, Pflugers Archiv Euro J Phys, 410: 296-303, which is hereby incorporated by reference). While those studies have been useful in exploring the signal transduction in the pelvic region, they are routinely performed using wire or hook electrodes to record from individually separated axons—an implementation that is not amenable to long-term patient care.

In addition to this sensory information, functional electrical stimulation (FES) of efferent pathways may provide a mechanism for the control of musculoskeletal and bladder, rectum, and sexual function after brain and spinal cord injury. Many current FES applications operate in open-loop mode, in which the intended function is not automatically regulated and no biological input is employed in modulating the stimulation. In closed-loop control, however, it is possible to change stimulation parameters dynamically in response to feedback from the peripheral organ or limb, enabling compensation for muscle fatigue and corrections to perturbations of the extremity. Continuous feedback control has yet to be fully implemented in FES applications due to challenges in the mounting, positioning, reliability, and inconveniences of external sensors, in addition to the need for wide variety of sensors for adequate detection of sensory input from a diversity of locations and organs. There is a growing interest to incorporate natural neural feedback into closed-loop FES systems. These approaches are currently limited by only recording from a single nerve bundle and are thus constrained to partial information and control of a limb or organ.

Electrical stimulation of afferent pathways can also be used to provide a mechanism for the control of bladder, rectum, and sexual function after brain and spinal cord injury, by leading to reflex activation of spinal circuits and efferent pathways. Stimulation of the pudendal nerve, or its distal branches, has been shown in animal and human studies to lead to reflex bladder excitation or relaxation (e.g., Tai et al., 2007 Neurourology and Urodynamics, 26: 570-7 and Gustafson et al., 2004 Neuroscience Letters, 360: 9-12, which are hereby incorporated by reference). Typically, this peripheral nerve stimulation can activate an entire nerve or nearby nerves and thus other undesired functions, such as concurrent urethral sphincter closure or painful sensations, may occur.

Peripheral stimulation to evoke reflex leg movements, which may assist individuals with loss of limb control, has also been demonstrated (e.g., Selionov et al., 2009, J Neurophysiology, 101: 2847-58, which is hereby incorporated by reference). However this stimulation approach is also non-specific. Stimulation of neural pathways can be used to block or mask propagation of unwanted signals, such as painful responses. Blocking of peripheral nerves with very high frequency stimulus patterns has been demonstrated (e.g., Ackermann et al., 2010, Muscle Nerve, 41: 117-119, which is hereby incorporated by reference), however this approach only targets a single peripheral nerve and thus can have a limited effect. Stimulation on the surface of the spinal cord can lead to paresthesias which mask painful sensations (e.g., Kumar et al., 1998, Surgical Neurology, 50: 110-121, which is hereby incorporated by reference), but a more selective approach that targets specific pathways may provide greater benefit.

EXAMPLES

The following examples are provided to illustrate particular features of certain embodiments, but the scope of the claims should not be limited to those features exemplified.

Example 1

Monitoring Bladder Pressure

This example illustrates use of an embodiment of a disclosed method for monitoring bladder pressure in a patient.

Microelectrode arrays were implanted into sacral DRG (S1 and S2) of cats to record neural activity from sensory afferents innervating the bladder and pelvic region to show that bladder afferent neural signals could be recorded and used to estimate bladder pressure. After appropriately anesthetizing the subject, a catheter was inserted intraurethrally to the bladder for controlling the bladder volume and measuring bladder pressure. The S1-S2 sacral DRG were exposed and penetrating microelectrode arrays (90 channels: 4×10 and 5×10 ICS-96 MultiPort split planar arrays, 1 mm shaft length, 0.4 mm interelectrode spacing, Blackrock Microsystems) were inserted in the S1 (4×10 array) and S2 (5×10 array) DRG on the left side of each cat with a pneumatic inserter (Blackrock Microsystems).

Neural data from the microelectrode arrays and the analogous bladder pressure were recorded using a biopotential processor for data sampling and storage (RZ2, Tucker Davis Technologies (TDT)). Neural signals were band-pass filtered (300-3000 Hz) and sampled at 25 kHz, with thresholding performed online to extract spike waveforms for offline analysis. The bladder pressure was sampled at 100 Hz and filtered offline (4 Hz low-pass). Neural signals from the S1 and S2 DRG were recorded while the bladder volume was controlled. First, constant bladder volume trials were performed. Starting at zero mL and continuing in 5-10 mL increments until the bladder leaked around the urethra catheter, one-minute constant bladder volume trials were recorded.

Offline analyses were performed to identify neural units that responded to changes in the bladder pressure. Spikes on each electrode channel were manually sorted in OpenSorter (TDT) and saved on a local storage drive. To identify bladder afferent units, a simple linear regression was performed between the averaged spike count in each constant bladder volume trial and the corresponding average bladder pressure. Units that showed a similar change in their firing rate across the tested bladder pressure range as reported for individual pelvic (Winter, *J. Psychiatric Research,* 8, August 1971, pp. 225-35; Iggo, *J. Physiology,* 128, 1955, pp. 593-607) and sacral root axons (Häbler et al. *J. Physiology,* 463, 1993, pp. 449-60) were identified as bladder units.

In trials with a bladder pressure range of at least 10 cm $H_2O$, a second regression model was created for estimating the bladder pressure. All DRG units were included in this model. Firing rates were calculated at 10 ms intervals, using a previously described linear filter (Weber et al., *J. Neural Engineering*, 4, 2007, p. S168-S180, incorporated by reference herein). A 1.5 s Gaussian kernel was used in the filter, because bladder pressure variations occur slowly and bladder units often fire less than once per second at low bladder pressures (Häbler et al. *J. Physiology*, 463, 1993, pp. 449-60, incorporated by reference herein). Data from the first and second halves of individual trials were parsed to form training and test periods (30-60 s for each). The linear correlation coefficients (ρ) between each individual unit and the bladder pressure were calculated for the calibration period. All units were ranked by their unsigned ρ value, in descending order. Next, data from the calibration period were used to identify coefficients in the following multivariate linear regression model:

$$\pi_i = a_0 + \sum_{j=1}^{N} a_j r_{i,j} \quad (1)$$

In (1), $\pi_i$ refers to an estimate of the bladder pressure (p) at time i, based on a weighted sum of the firing rates ($r_{i,j}$) of N neurons at that instant. The coefficients ($a_x$) are determined from a least-squares fit. The fitted model was then used to estimate bladder pressure in the test period data. The regression fit and estimate was performed using population sizes (N) ranging from one to the total number of identified units, starting with the first unit in the list of neurons rank-ordered by their correlation (ρ) with bladder pressure.

The root mean square error (RMSE) between each regression period and the measured bladder pressure was calculated by (2).

$$RMSE = \sqrt{\frac{\sum_{i=1}^{t}(p_i - \pi_i)^2}{t}} \quad (2)$$

In (2), $p_i$ and $\pi_i$ refer to the measured and fitted/estimated bladder pressure at time i across the t data points. The correlation coefficient (ρ) between the estimated bladder pressure and measured bladder pressure during the test period was also calculated.

Figure 2A:
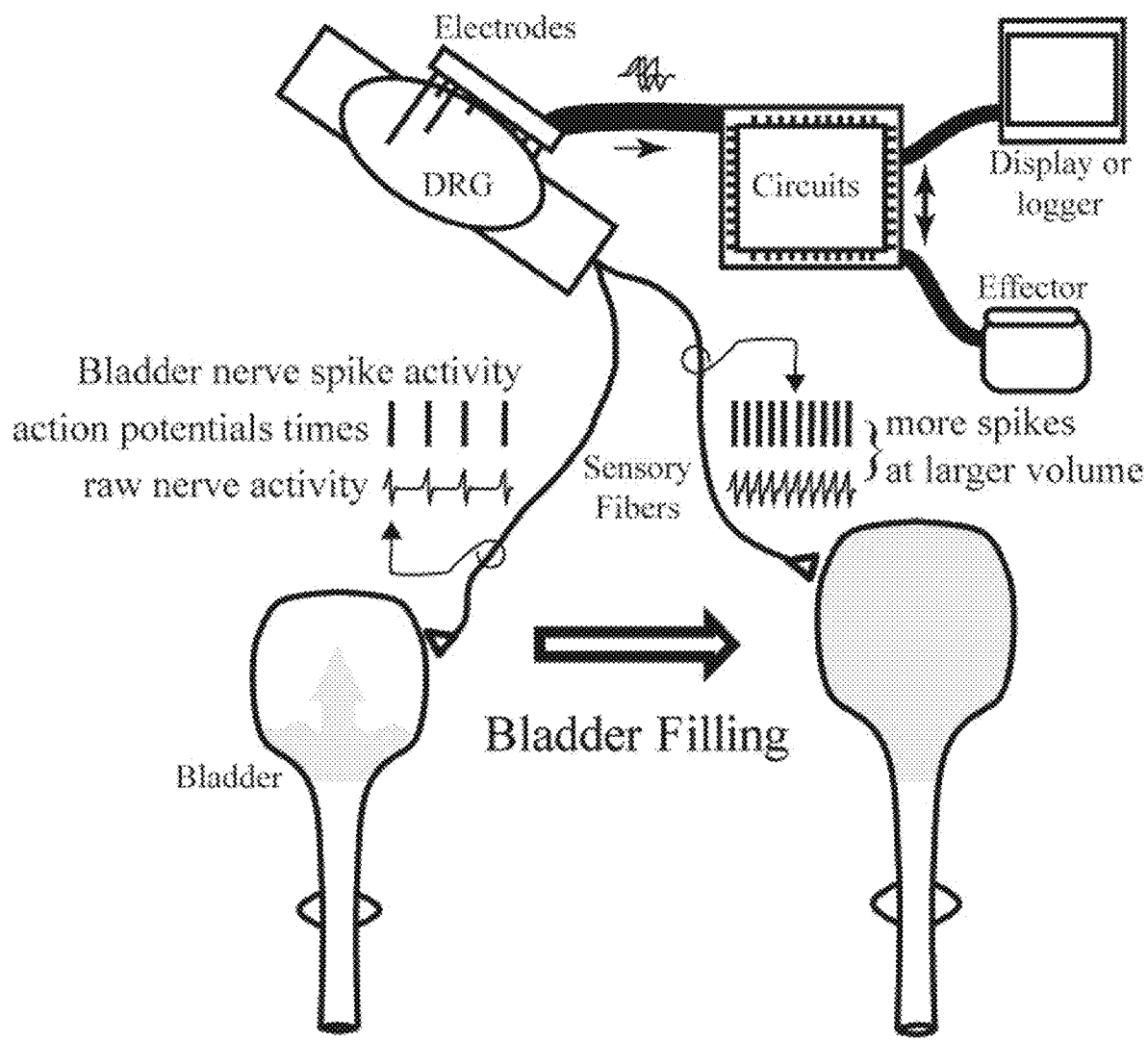
FIGS. 2A-2C show a schematic diagram illustrating a disclosed apparatus used for monitoring DRG neuronal activity associated with bladder activity (FIG. 2A), a set of charts displaying recordings of DRG neuronal activity associated with bladder activity and correlated with bladder pressure using a disclosed monitoring apparatus (FIG. 2B), and a chart showing an estimate of bladder pressure from DRG neuronal recording using a regression model using activity of five DRG cells in a disclosed method (FIG. 2C). The chart in FIG. 2C demonstrates the utility of the measurements of a disclosed method in predicting bladder fullness.
Figure 2B:
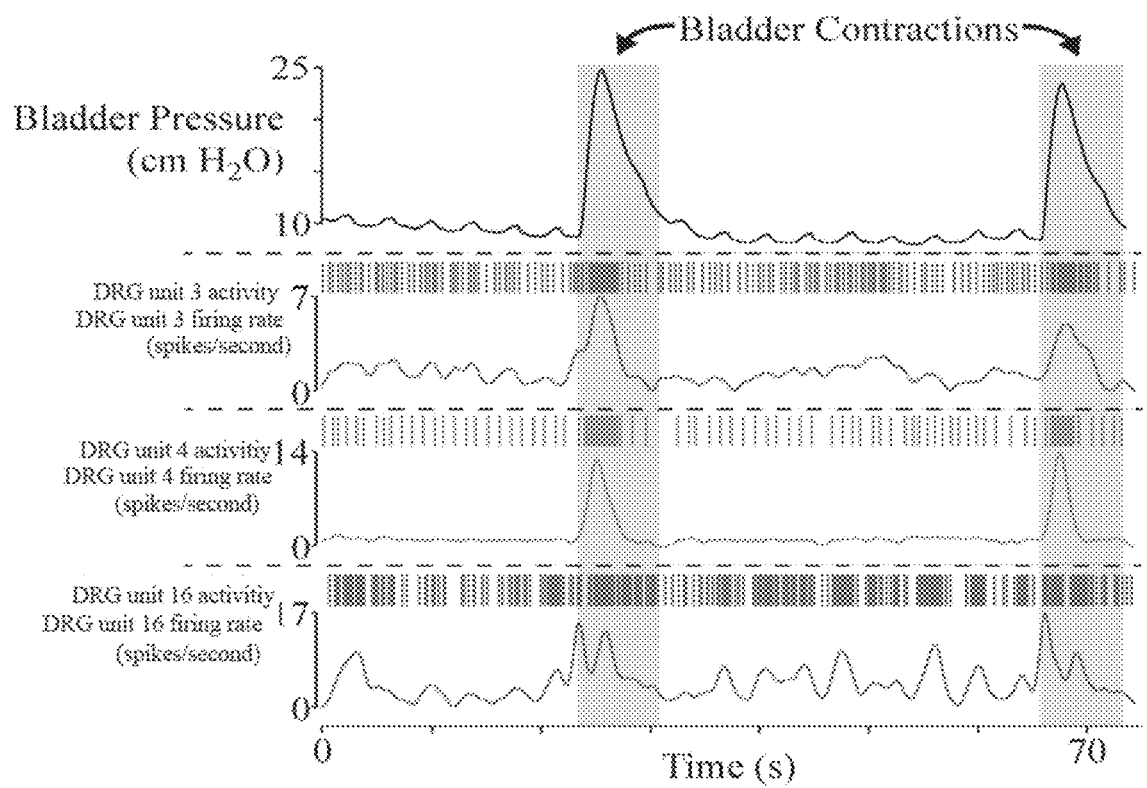

In each of two experiments, bladder units were identified from sacral DRG recordings and accurate estimates of the bladder pressure were obtained using only a few DRG units (average bladder pressure estimate errors of 3.0-3.2 cm $H_2O$). Six DRG units in each cat were identified as bladder units, with a majority in S2 (4 in first cat; 6 in second cat). The bladder units exhibited no spiking activity when the bladder was empty and had mean firing rates between 2 and 8 spikes per second (15 spikes per second max) at pressures above 30 cm $H_2O$. FIG. 2B shows the firing rates of two bladder DRG units exhibiting a high correlation with bladder pressure and a third unit that was more weakly correlated during two small bladder contractions. Similar DRG recordings have been demonstrated from other pelvic organs, such as the urethra and rectum.

Figure 2C:
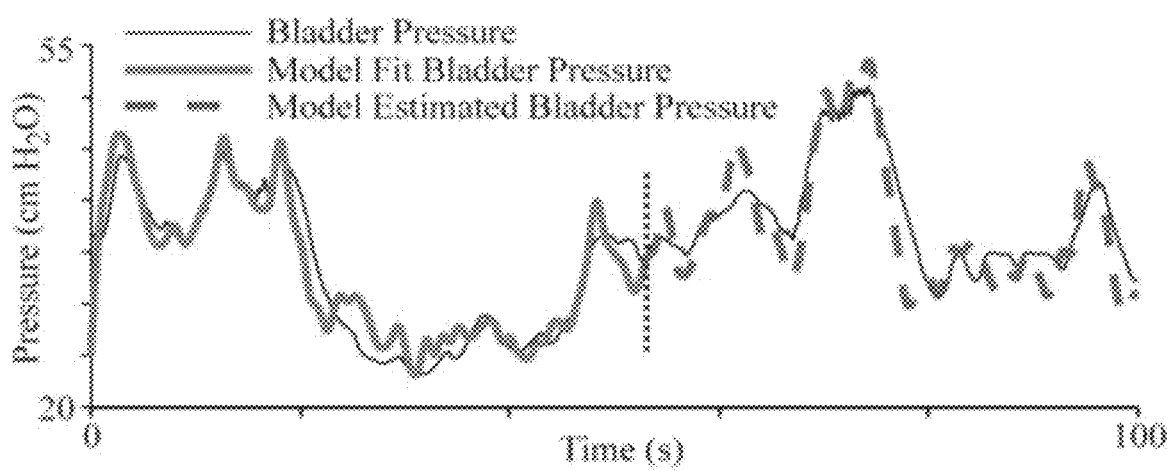
Figure 3A:
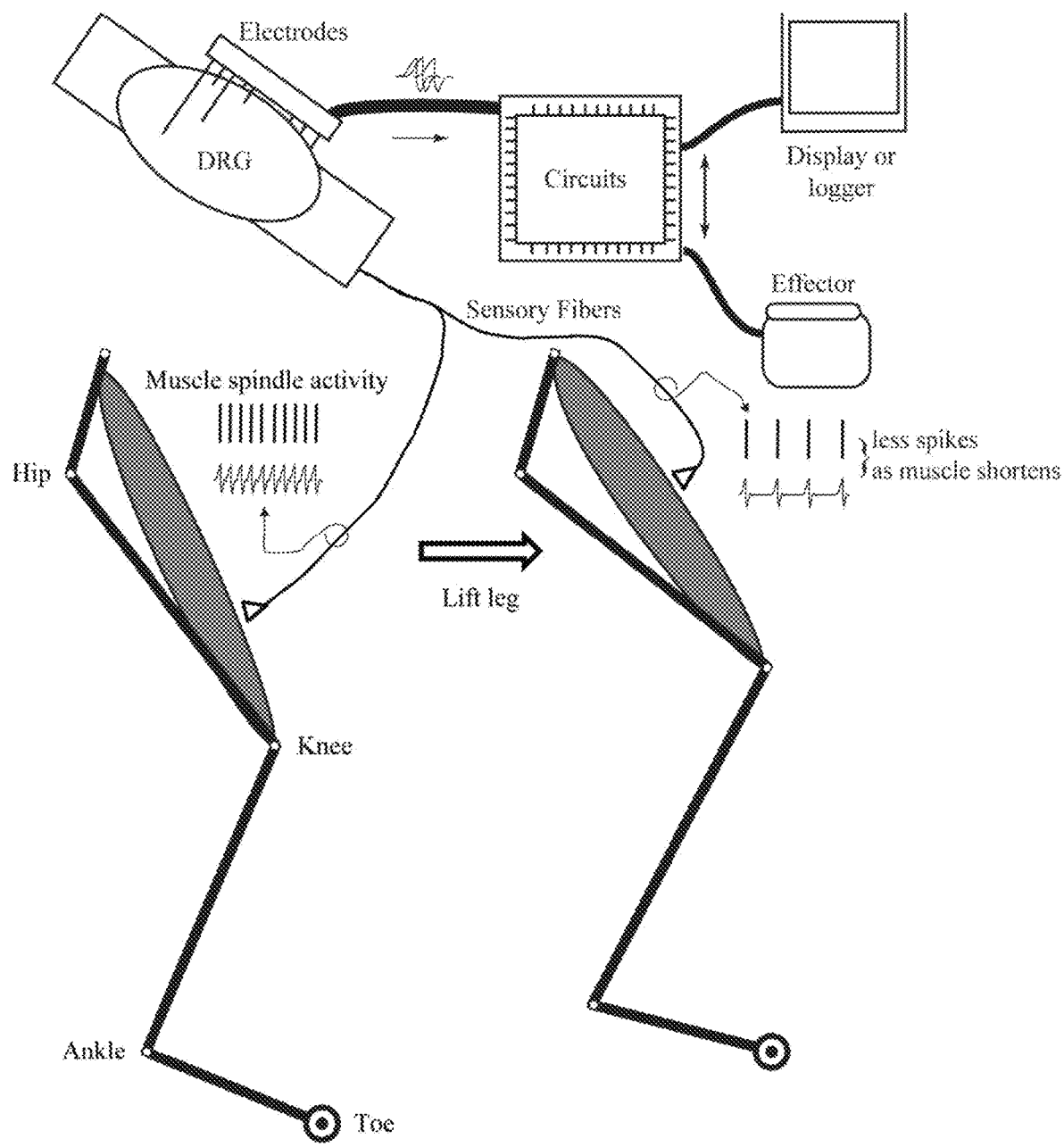
FIGS. 3A and 3B shows a schematic diagram of a disclosed apparatus used for DRG recording of limb activity (FIG. 3A), and a set of charts displaying recordings of DRG neuronal activity associated with limb movement and correlated with hip angle using a disclosed monitoring apparatus (FIG. 3B).
Figure 3B:
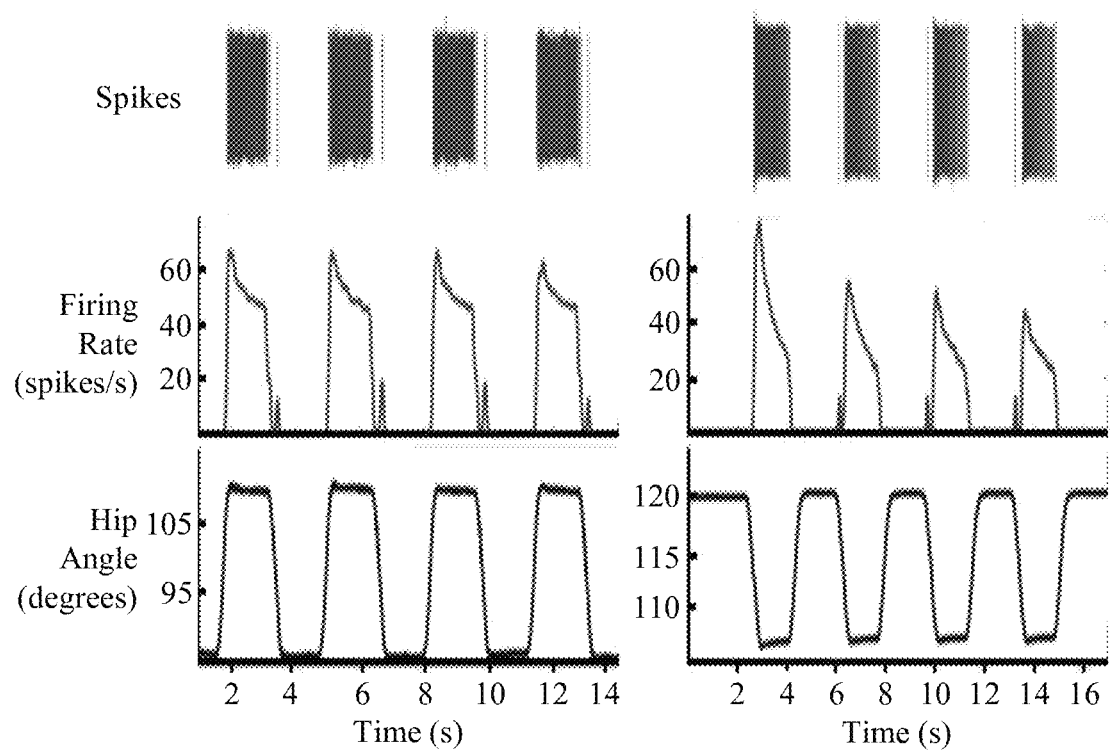

FIG. 2C shows the monitoring of bladder pressure utilizing an embodiment of a disclosed apparatus. The firing rates of 5 DRG units were entered into a simple linear regression model described above. In the first half of the trial a regression model was created and fit to the bladder pressure using standard statistical techniques. In the second half of the trial the DRG unit firing rates were used to estimate the bladder pressure with high accuracy (ρ=0.88). This example demonstrates how the bladder pressure can be estimated in real time from the activity of identified DRG neurons.

A DRG microelectrode interface has several advantages over whole-nerve approaches. Recording from DRG units yields a higher resolution for bladder contractions, as individual units have clear increases in firing rates (FIG. 2B) as compared to low signal-to-noise ratios and/or sub-microvolt changes in whole-nerve electroneurograms. A DRG interface with individual bladder units would monitor slow pressure changes with greater accuracy than whole-nerve approaches, which typically only reveal phasic activity or gradual changes at higher pressures. Tracking bladder activity with DRG bladder units will likely have a lower false positive rate for indicating bladder contractions than whole nerve approaches which are not selective for non-bladder activity, as DRG units for other pelvic functions may be identified and also monitored.

Example 2

Monitoring Limb Movement

This example illustrates use of an embodiment of a disclosed method for monitoring limb movement in a subject. A monitoring apparatus as described in Example 1 was applied to an animal model (a cat) for in vivo DRG recordings from two muscle spindles in lumbar DRG that signal the length of the muscles around the hip are shown in FIG. 4B. The firing rate of these neurons in the DRG reflects the state of the muscle.

Example 3

Stimulation of Bladder, Limb and Cortical Neuron Activity

This example illustrates use of an embodiment of a disclosed method of stimulating DRG neurons to activate a sensory neuron reflex circuit that induces bladder function in a subject.

Bladder Activity

Figure 5A:
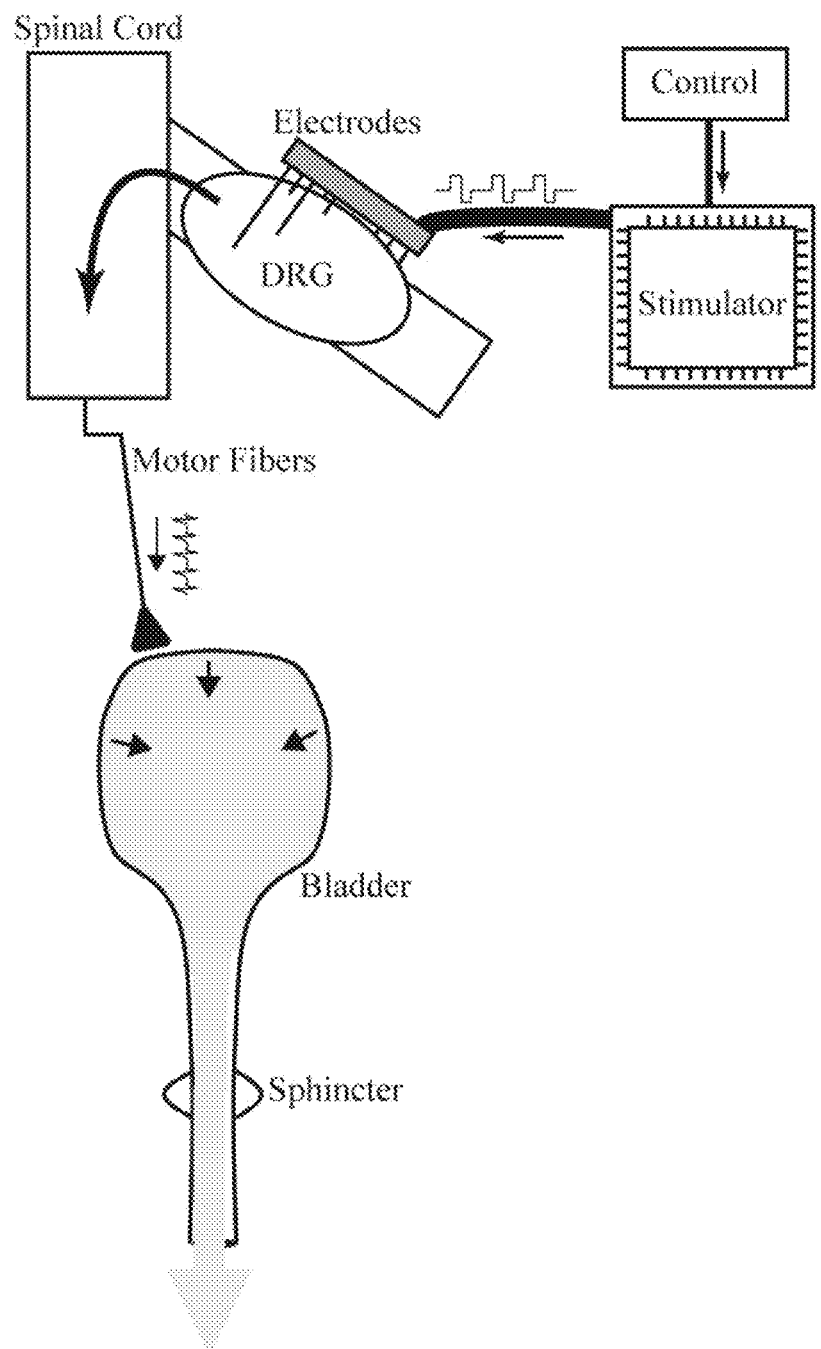
FIGS. 5A and 5B show a schematic diagram illustrating a disclosed apparatus used for stimulating DRG neuronal activity to activate a sensory neuron reflex circuit that elicits bladder activity (FIG. 5A) and a graph displaying bladder pressure regulated by stimulation delivered to different electrodes in the DRG (FIG. 5B). The data in FIG. 5B show that an embodiment of a disclosed method can be used to induce excitation of the bladder.
Figure 5B:
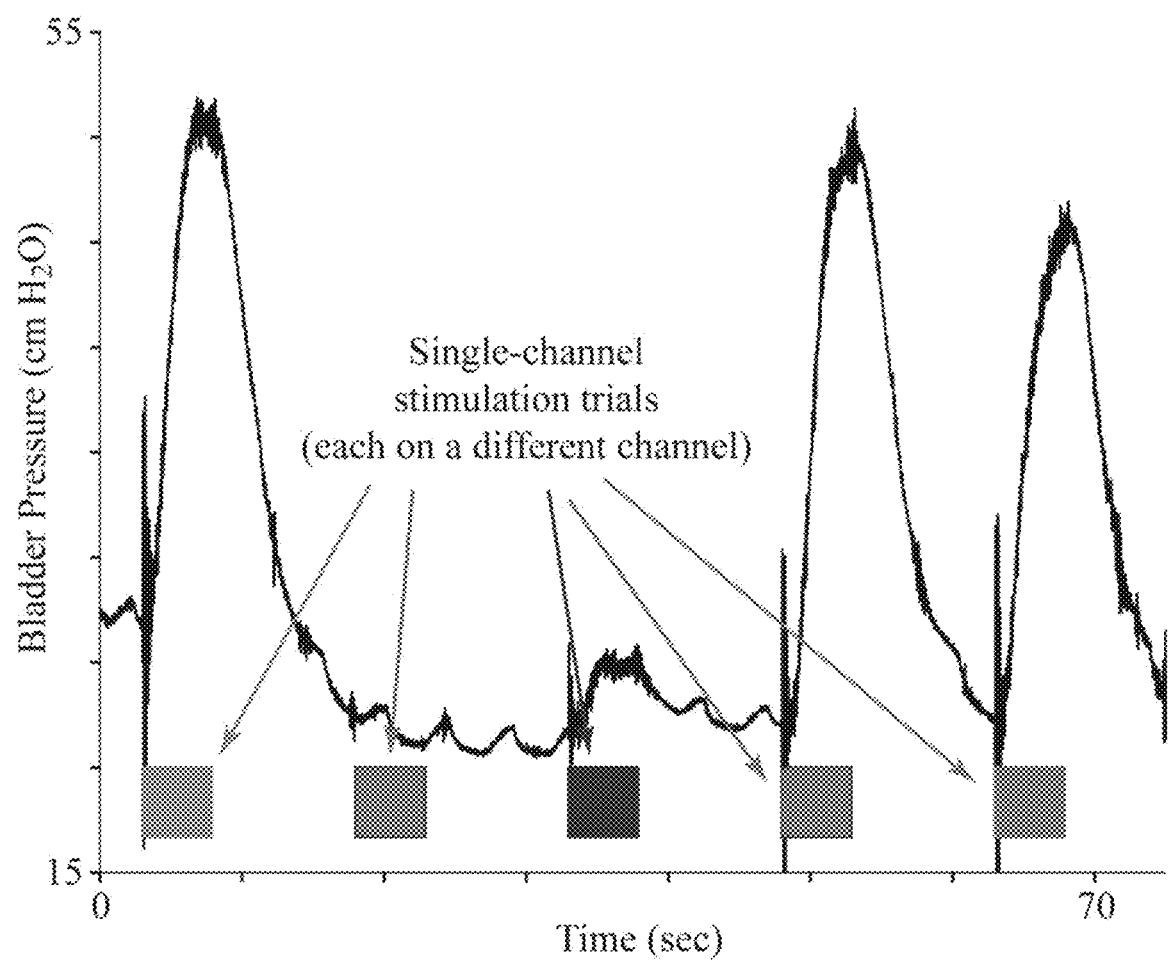

Experiments utilizing cats were performed to demonstrate that stimulation through electrodes on a microelectrode array inserted into a sacral DRG can cause the bladder to contract or relax. In these experiments, stimulation through a single microelectrode or multiple microelectrodes in the same DRG, with stimulation frequencies below 100 Hz and current levels below 100 µA, was able to evoke reflexive bladder responses. FIG. 5B shows data collected from a cat in which targeted DRG stimulation causes bladder excitation (set up illustrated in FIG. 5A). There, a microelectrode was inserted into the S1 DRG of a cat. Each microelectrode was individually stimulated for 5 seconds at 30 Hz and 50 µA. Some microelectrodes strongly recruited the bladder ($1^{st}$, $4^{th}$, $5^{th}$ electrodes) while others did not excite the bladder ($2^{nd}$, $3^{rd}$ electrodes). This experiment demonstrates how targeted stimulation of DRG cells can elicit a response without needing to stimulate the entire DRG or nerve bundle as is typically done in the prior art.

Figure 6A:
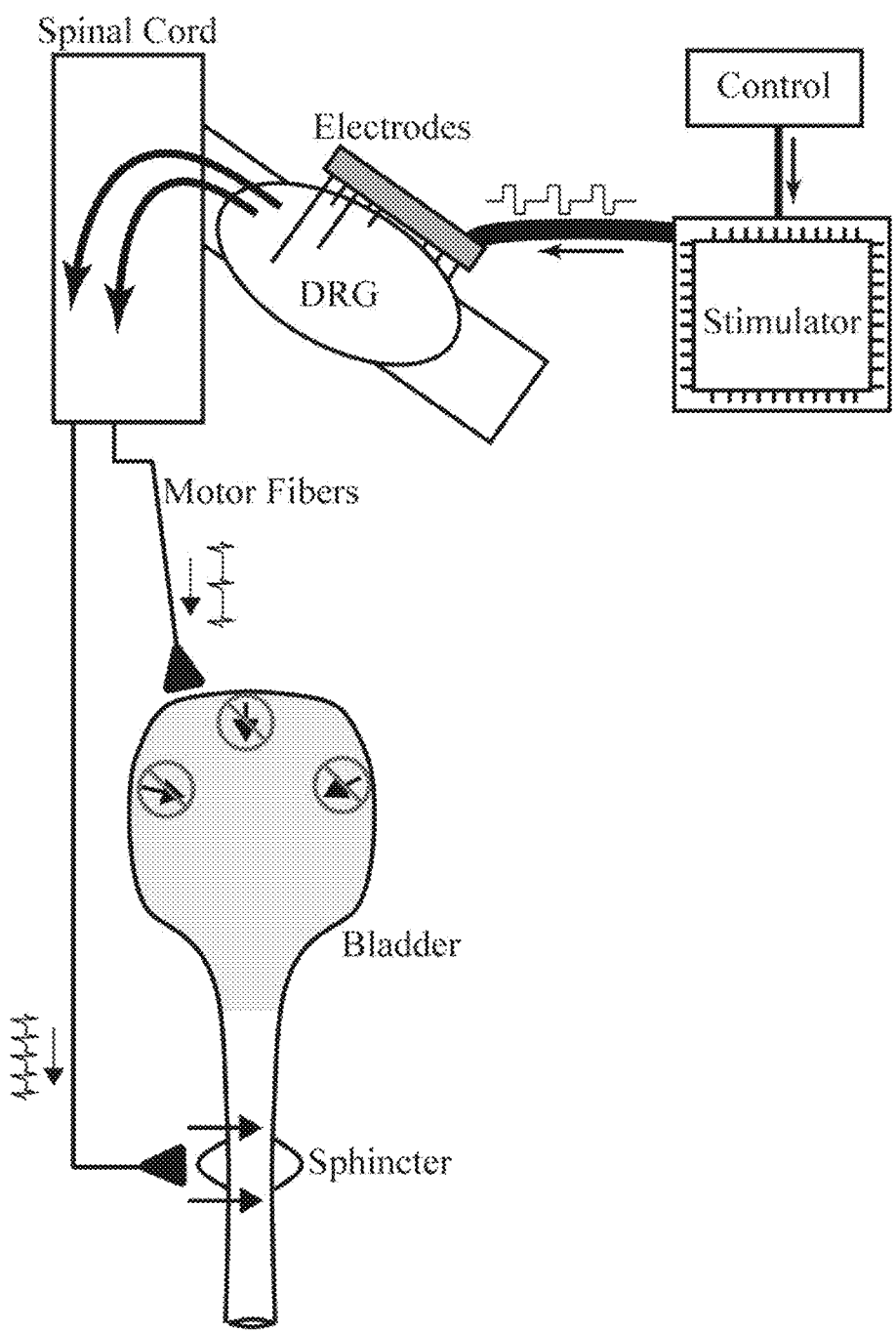
FIGS. 6A and 6B show a schematic diagram illustrating a disclosed apparatus used for stimulating DRG neuronal activity to activate a sensory neuron reflex circuit that inhibits bladder activity (FIG. 6A) and a graph displaying bladder pressure relaxed by DRG stimulation (FIG. 6B).
Figure 6B:
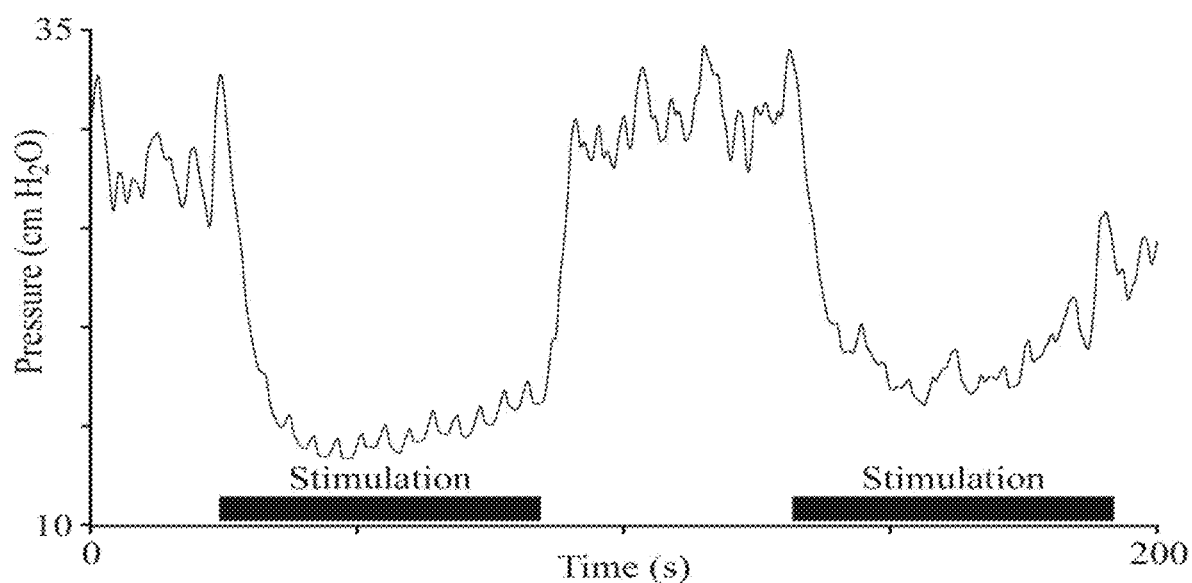

FIG. 6B displays data from an experiment in which electrical microstimulation of DRG neurons achieved bladder inhibition (set up illustrated in FIG. 6A). There, microelectrode channels inserted in the S2 DRG were stimulated at 5 Hz with 10 µA while the bladder pressure was high (above 25 cm H$_2$O). This stimulation pattern led to a clear relaxation of the bladder, showing activation of a continence reflex through targeted DRG microstimulation.

Hind Limb Activity

Figure 7A:
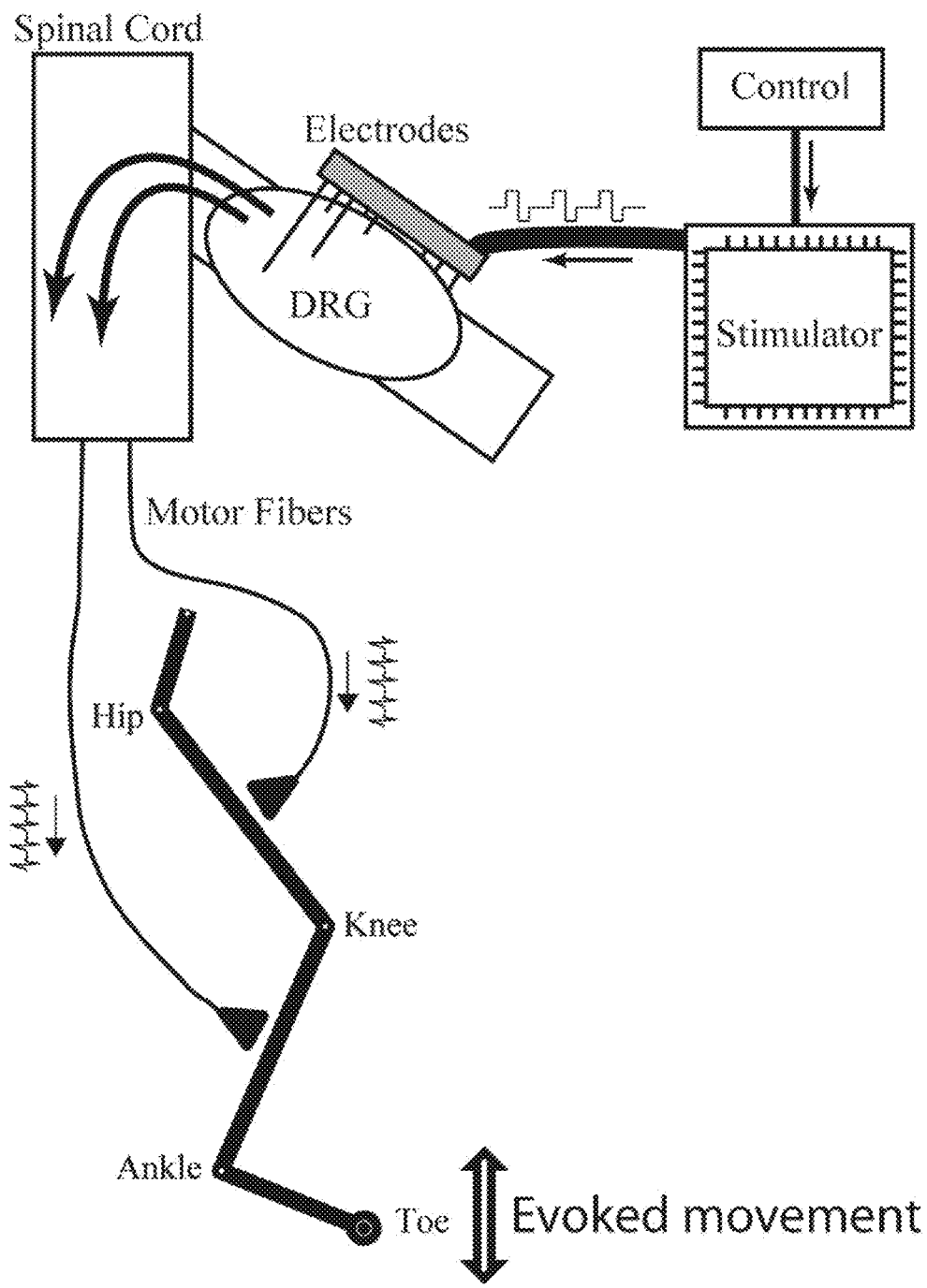
FIGS. 7A and 7B show a schematic diagram illustrating a disclosed apparatus used for stimulating DRG neuronal activity to activate a sensory neuron reflex circuit that regulates lower limb movement (FIG. 7A) and a chart showing excitation of flexor or extensor muscles of the leg induced by DRG stimulation (FIG. 7B).
Figure 7B:
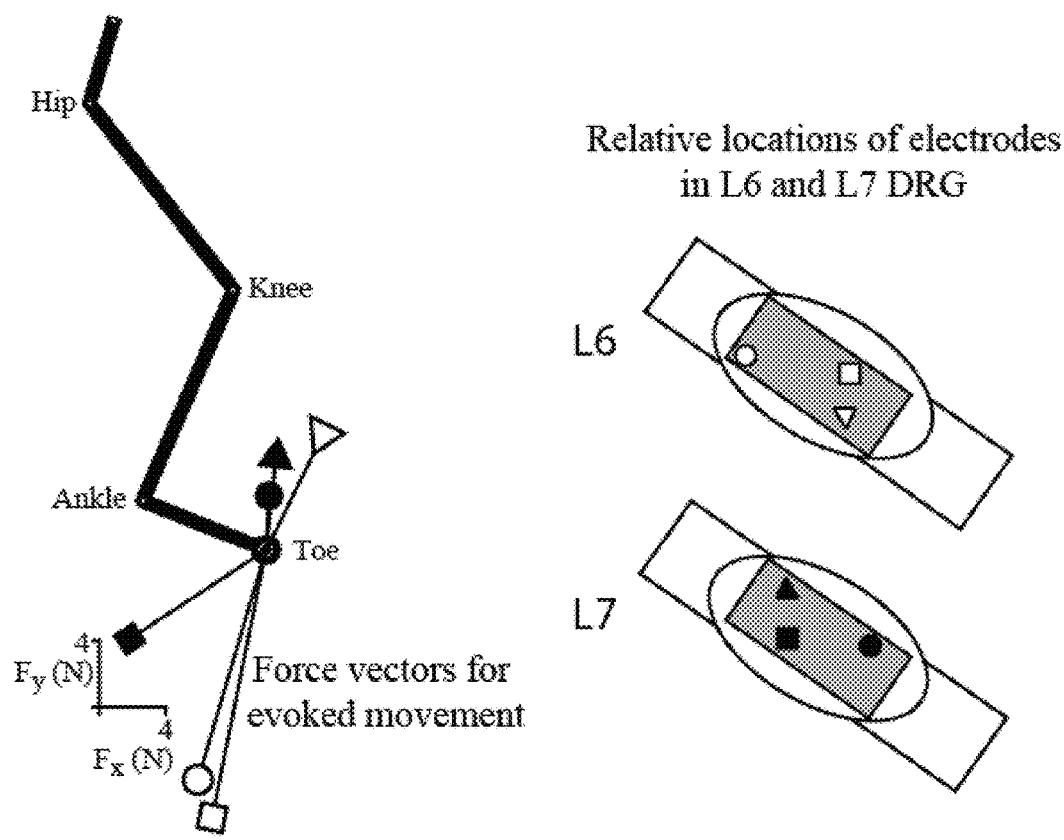

FIG. 7B displays data from an experiment in which electrical microstimulation of DRG neurons resulted in activation of flexor and extensor muscles of the hind leg (set up illustrated in FIG. 7A). The symbols indicate the direction and amplitude of maximum force vectors evoked by DRG stimulation in anesthetized cats. Each stimulus channel is represented by a different symbol. There was no discernible difference in force directions between stimulation in L6 (open symbols) and L7 (filled symbols). This also demonstrates that microstimulation at different targeted DRG elicit reflex responses appropriate for the stimulated DRG.

Sensory Responses in the Brain

Figure 8A:
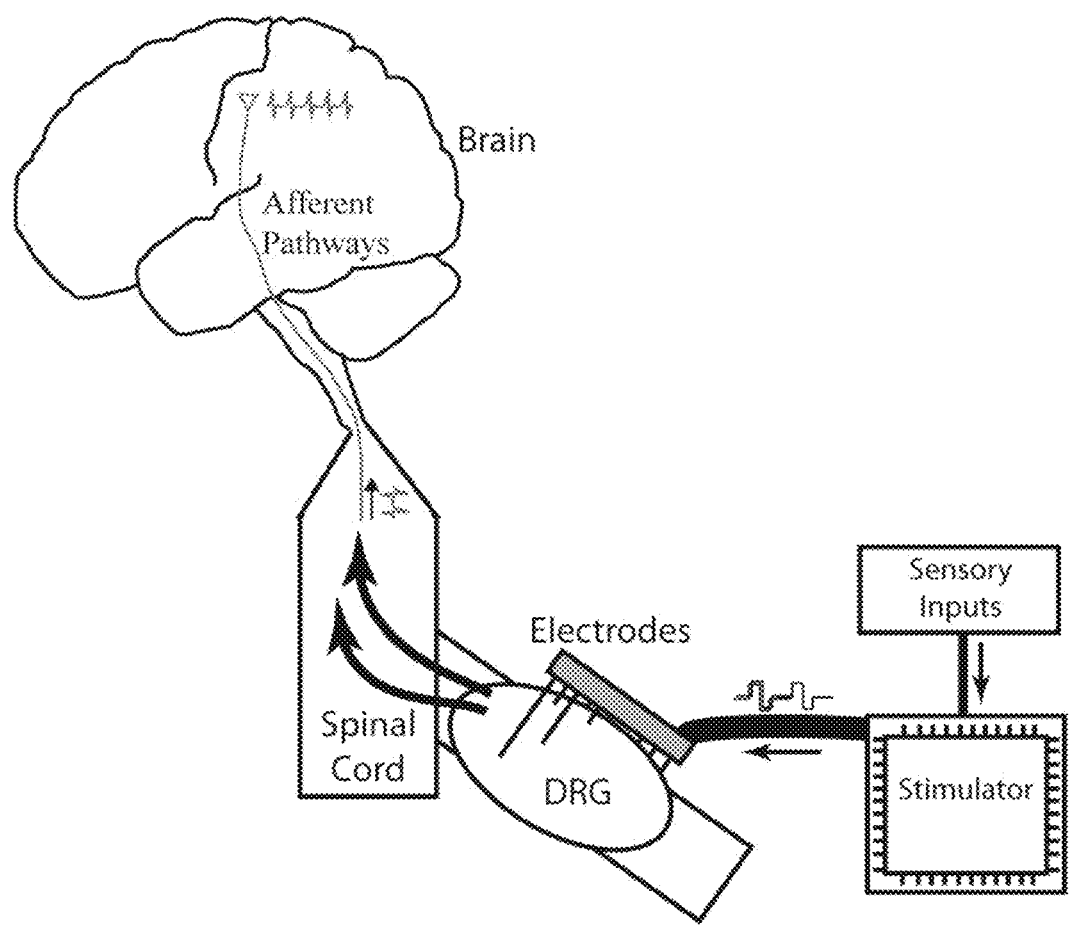
FIGS. 8A and 8B show a schematic diagram illustrating a disclosed apparatus used for stimulating DRG neuronal activity (FIG. 8A) and recordings of cortical neuron activity induced by DRG stimulation using the disclosed apparatus, as well as cortical neuronal activity induced by limb movement and DRG stimulation (FIG. 8B). The correlation of cortical neuronal activity induced by DRG stimulation with cortical neuronal activity induced by limb movement is indicated. The data show that stimulation of DRG neurons using an embodiment of a disclosed method evokes naturalistic responses from cortical neurons in the brain, indicating that DRG stimulation may be used to restore tactile sensations or proprioception in persons with prosthetic limbs.
Figure 8B:
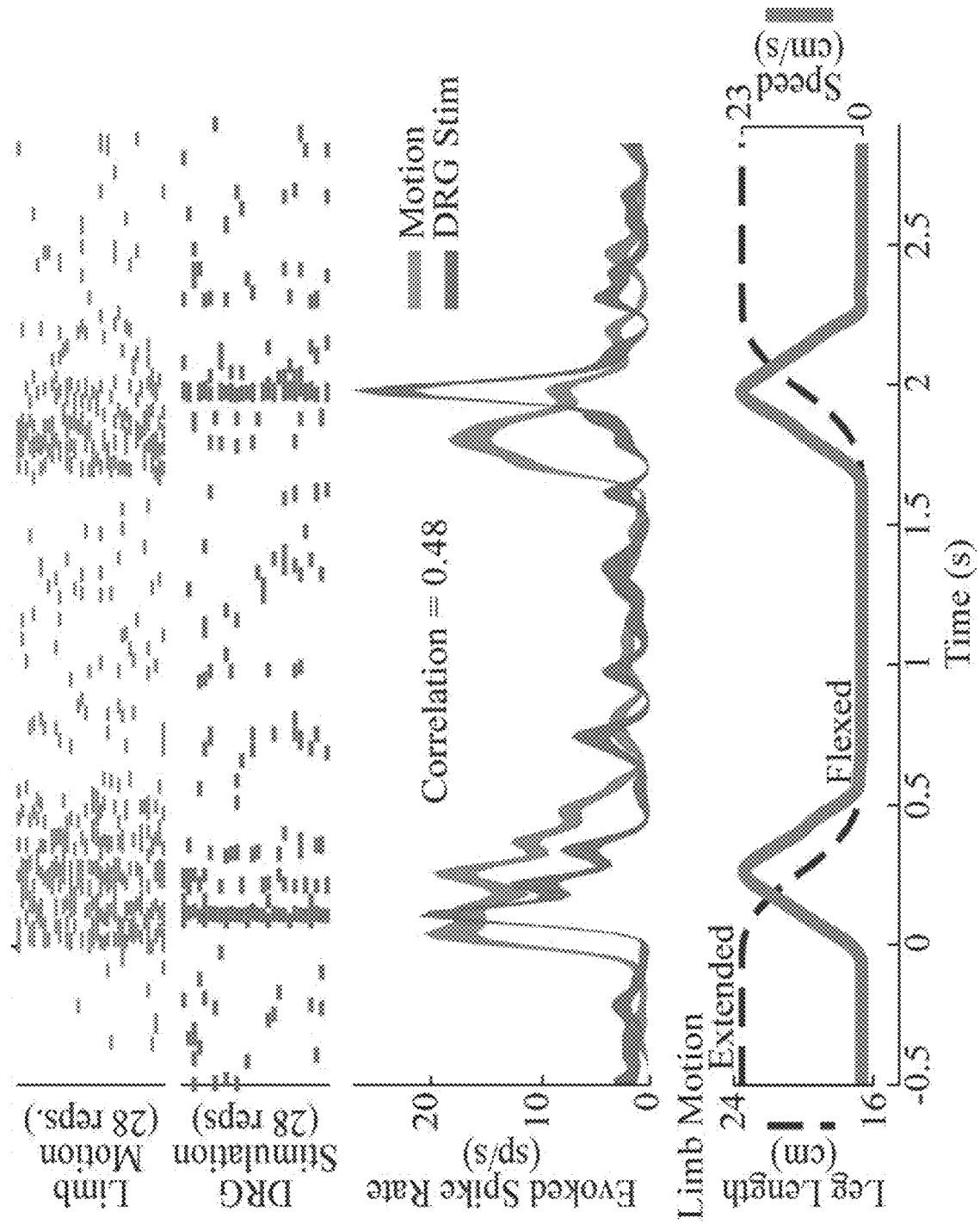

FIG. 8B displays data from an experiment in which electrical microstimulation of DRG neurons evoked responses in the brain that were similar to those evoked by leg movement (set up illustrated in FIG. 8A). The tick marks in the top two plots show the pattern of neural spiking activity (each tick represents the occurrence of a neural spike) in the sensory cortex of the brain during leg movement (top panel) and during electrical stimulation (second panel) through patterns of microstimulation in the DRG. The third panel shows the instantaneous spike rates for the sensory cortex neuron during the motion and stimulation trials. The bottom panel shows the position and speed of the foot as the leg was moved from an extended position to a flexed position and then back to an extended position during the motion trials. This example shows that the response evoked in the brain during microstimulation in the DRG was similar to that during natural movement of the limb.

Example 4

Control of Hind Limb Functional Electrical Stimulation Using Feedback from DRG Recordings This example illustrates that primary afferent recordings from lumbar DRG provide sufficient information for closed-loop control of the limb. Functional electrical stimulation (FES) approaches for limb control typically operate using open loop stimulation sequences and are unable to adapt automatically to muscle fatigue and perturbations. This example illustrates that kinematic feedback decoded from DRG unit activity can be used to perform closed-loop control of FES enabled stepping. It is demonstrated that real-time closed-loop FES control of a hind limb utilizing limb position estimates decoded from the spike counts of DRG neurons. Multi-state walking patterns with a closed-loop controller that discarded stimulation artifacts and responded appropriately to perturbations in the desired limb path were successfully generated.

Figure 9A:
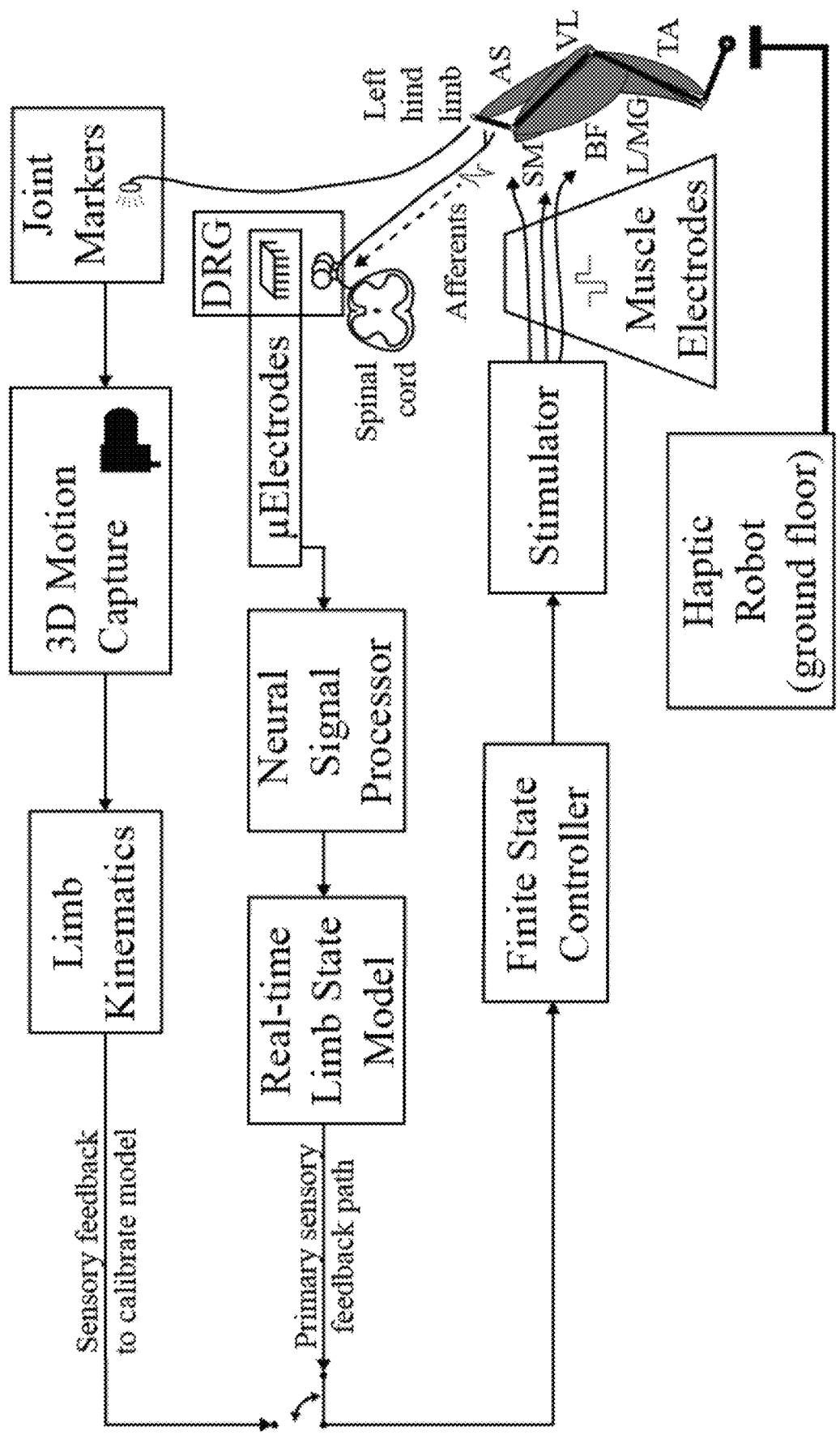
FIGS. 9A and 9B shows a schematic diagram of an embodiment of a disclosed apparatus for monitoring DRG activity to provide closed loop feedback for functional electric stimulation of lower limb movement and the major muscle groups targeted for stimulation.

One to three stimulating electrodes were inserted into each of the primary flexion and extension muscle groups of the left hind limb joints of a cat: anterior sartorius (hip flexion), semimembranosus (hip extension), biceps femoralis (knee flexion), vastus lateralis (knee extension), tibialis anterior (ankle flexion) and lateral and/or medial gastrocnemius (ankle extension). FIG. 9A illustrates the overall setup and the major muscle groups targeted for stimulation.

As shown in FIG. 9A, an array of microelectrodes in the L6 and L7 DRG monitored sensory afferents from the left leg. Neural signals were acquired by a neural signal processor and sent to a PC running software to estimate the limb position in real-time. State estimates were updated every 50 ms and sent to a finite state controller also running on the PC, which controlled the FES system. Muscle electrodes targeted the anterior sartorius (AS; hip flexion), semimembranosus (SM; hip extension), biceps femoralis (BF; knee flexion), vastus lateralis (VL; knee extension), tibialis anterior (TA; ankle flexion) and lateral or medial gastrocnemius (L/MG; ankle extension). A haptic robot generated forces resisting extension of the limb, to simulate ground contact mechanics. A motion capture system and active joint markers on the iliac crest, hip, knee, ankle and toe also tracked the position of the limb. Each muscle was exposed during surgery and electrodes were placed on or in the muscle belly. A needle inserted percutaneously in the abdomen or ipsilateral foot served as the return electrode.

After revealing the spinal laminae by reflecting the paraspinal muscles overlying the L5-S1 vertebrae, a laminectomy was performed to expose the lumbar DRG (L5-S1) on the left side. The cat was placed in a custom frame, which supported the torso, spine and pelvis while allowing the hind limb to move freely. Microelectrode arrays were inserted into the L6 and L7 DRG (10×4 and 10×5, respectively) with a pneumatic inserter and the wire bundles were secured to the dura with suture. A bone screw in the iliac crest was used as a ground electrode, and a recording reference wire was placed near the spinal cord.

Neural signals from the microelectrode arrays were recorded with a signal processing system at 25 kHz and band-pass filtered (300-3000 Hz). An amplitude threshold was set on each electrode channel above the noise floor and a spike event was stored each time this threshold was crossed. A spike event consisted of a time stamp and a snippet of voltage data representing the spike waveform (0.7-1.2 ms duration). Spike-sorting of the waveforms on each channel was performed on the neural processor using principal components analysis and K-means clustering (K set to 2). Before attempting FES, the clusters were manually verified and combined into a single cluster when the clusters represented the same afferent or both clusters contained multi-unit activity.

During FES, stimulation artifacts were removed using a dual approach. Most artifacts were automatically rejected by the clustering algorithm. In addition, a simple artifact rejection algorithm was implemented in the neural processor, as described Bauman et al., 33rd Annual International Conference of the IEEE Engineering in Medicine and Biology Society, 2011, pp. 7246-7249, incorporated by reference herein. Briefly, if the sum of spike-threshold crossing events across all channels during a 400 μs detection window exceeded a set limit (54 channels; 60%) then all events in a corresponding 2 ms rejection window were excluded from the spike count vector. Since active electrodes were stimulated synchronously at 30 Hz, this rejection window retained over 90% of time available for neural decoding.

For each sorted unit, after artifact rejection, the neural processor calculated spike counts ($C_i$) in 50 ms bins. A spike count vector ($SC_i$) for each unit was generated by smoothing counts over prior time points, as indicated by equation (1).

$$SC_i(v) = \frac{C_i(v)}{2} + \frac{C_i(v-1)}{3} + \frac{C_i(v-2)}{6} \qquad (1)$$

In equation (1), v is a time index corresponding to 50 ms time bins for the spike count calculation of neuron i. This smoothing approach was selected to reduce jitter in the spike count vector.

Figure 9B:
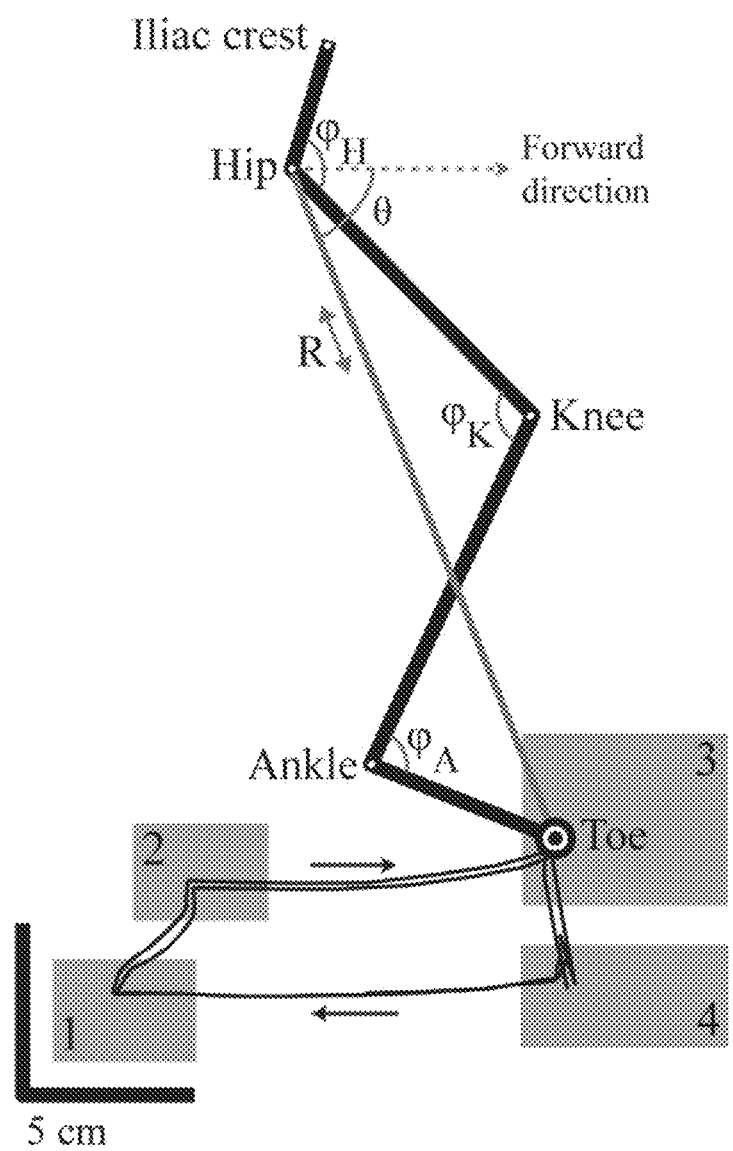

Active LED markers were placed over the left iliac crest and the hip, knee, ankle joints and toes. The marker locations were recorded with a 6-camera motion capture system, sampled at 120 samples per second. A software program was used to calculate the hip, knee and ankle joint angles from the marker locations in real-time. As in previous studies, the limb position was represented in two reference frames (FIG. 9B). Intersegmental angles were used to measure the angular position of the hip ($\varphi_H$), knee ($\varphi_K$), and ankle ($\varphi_A$) joints. Segment lengths for the femur, shank, and foot were measured and combined with the joint angle measurements to determine the position of the toe relative to the hip. The toe position relative to the hip expressed as a vector in polar coordinates was also measured. The length of the vector was the hip to toe distance (R) and the orientation of the vector ($\theta$) was measured with respect to the horizontal. For simplicity, the 3 joint and 2 endpoint position variables were included in a single state vector ($X_m$; m=1,2,3 for hip, knee, and ankle angles, m=4,5 for hip-to-toe distance and orientation angle). A haptic robot was attached to the plantar surface of the left foot and programmed to create a virtual floor, rendering ground reaction forces during the stance phase of a step cycle (transition from state 4 to state 1 in FIG. 9B).

A multivariate linear regression model was used to estimate the limb position as a function of the ensemble neural spike counts (see Weber et al., *IEEE Transactions on Neural Systems and Rehabilitation Engineering*, 14, pp. 240-243, 2006; Weber, J. Neural Engineering, vol. 4, no. 3, pp. S168-S180, 2007 for a description of the regression model). All observed DRG units were included in the regression model. The estimated hind limb joint angles ($X^*_m$; m=1, 2, 3 for hip, knee, ankle) and the hip-to-toe distance and angle with the horizon (m=4, 5) were obtained from equation (2).

$$X^*_m = \hat{\beta}_{m0} + \sum_{i \in S_N} \hat{\beta}_{mi} SC_i \quad (2)$$

In equation (2), $S_N$ refers to the set of N units that were sorted in real-time by the clustering algorithm and $\hat{\beta}_{mx}$ are the least-squares estimates of regression coefficients.

A custom finite state controller was developed that modified the stimulation parameters based on the location of the hind limb endpoint. The controller used the actual toe position ($X_m$), measured by the motion-capture system, or the estimated toe position ($X^*_m$) based on the neural recording to update the stimulation parameters.

The controller operated in one of four distinct states based on the current position of the toe. The four states corresponded to different phases of the step cycle. In state 1, the controller stimulated the ankle and knee flexor muscles to lift the leg. In state 2, the hip and ankle flexors were activated to move the foot forward. In state 3, the hip flexors remained active while the ankle and knee extensor muscles were stimulated to plant the foot on the virtual floor rendered by the haptic robot. Finally, in state 4, the hip, and ankle extensors were stimulated to pull the leg backwards (against the virtual ground).

State-switch regions were defined as boxes in the four quadrants of the expected range of motion of the hind limb. As needed, the dimensions of each state region box were adjusted to match the range of motion that could be achieved during each phase of the stimulation cycle. At each time point (50 ms increments) the position of the toe was evaluated and a state change was triggered when the toe position entered one of the pre-determined state-switch regions (see FIG. 9B). This closed loop control scheme cycled through different stimulation states, resulting in a stepping motion.

To configure the stimulation parameters, the threshold current for muscle twitch recruitment for each electrode was first determined. Next, groups of muscles were stimulated simultaneously to generate coordinated limb movements for each phase of a stepping cycle. Muscle stimulation amplitudes (0.5-20 mA) were adjusted manually to achieve the desired movement. The stimulation waveforms were charge-balanced cathodal-leading stimuli with a half-amplitude recovery phase at a fixed stimulation frequency (30 Hz) and pulse width (200 µs). Current levels for each stimulating channel were controlled individually, in multiples of the respective threshold current.

During a calibration phase, the controller used the actual limb state (obtained by the motion capture system) to update the finite state controller. The stimulation parameter sequence drove the hind-limb through each of the four identified gait states. This resulted in closed loop FES control where the feedback was provided using the camera setup (see alternate feedback path in FIG. 9A). Estimates of the regression coefficients ($\hat{\beta}_{mx}$) were updated every 200 ms throughout the calibration phase using the smoothed spike count vectors ($SC_i$) and the recorded limb kinematics ($X_m$). The calibration phase was terminated when the estimated coefficients stabilized, which typically took 1-2 minutes.

Next, the predictions of the limb state ($X^*_m$) based on DRG afferent activity were used as feedback for the finite state controller. Here, the estimated toe position was inferred from the observed spike counts ($SC_i$) by equation (2) at 50 ms intervals. In the first experiment (cat I), a joint angle ($X^*_{1,2,3}$) reference frame was used to estimate limb position from the afferent firing rates, and used to calculate toe position. In the last experiment (cat K), the toe position in polar coordinates ($X^*_{4,5}$) was estimated directly from the afferent firing rates. For the purpose of decoding toe position during stepping, both reference frames can be used somewhat interchangeably as the firing rates of many primary afferent neurons correlate strongly with limb movements represented in both reference frames.

Before activating the closed loop FES, the hindlimb would be in resting position, typically hanging between states 4 and 1. When the controller was turned on, the initial target state was 1. Subsequently, the controller drove the limb from state to state to generate a complete step cycle (duration ~2-5 seconds per step). Approximately 10-15 step cycles were performed in each trial, with 5-15 minute rest periods between trials.

Subsequently, perturbation trials were performed in which the limb was obstructed to prevent movement to the next state transition zone. In one experiment, the foot was held manually for ≤2 seconds before being released. In another experiment, the haptic robot was programmed to generate a force simulating a virtual barrier for one second once the limb entered state 2. After that fixed time period, the virtual barrier was removed. The period of time that the barrier actually impeded the leg movement varied, as it was located between states 2 and 3.

The root mean square error (RMSE), as calculated in equation (4), was used to determine the error in limb position estimates.

$$RMSE = \sqrt{\frac{\sum_{u=1}^{t} (P_u - P^*_u)^2}{t}} \quad (4)$$

In (4), $P_u$ and $P^*_u$ refer to the measured and estimated hip-to-toe position at time u across the t data points in a trial. Where relevant, data is reported as average±one standard deviation.

Limb position was estimated in real-time while rejecting stimulation artifacts and demonstrated multi-state closed-loop control of a hind limb with FES in two cats (I, K). These results show the feasibility of estimating the limb position in real-time from the decoded activity of DRG units and integrating the limb position estimates into closed-loop control of FES for rudimentary locomotion.

Figure 10:
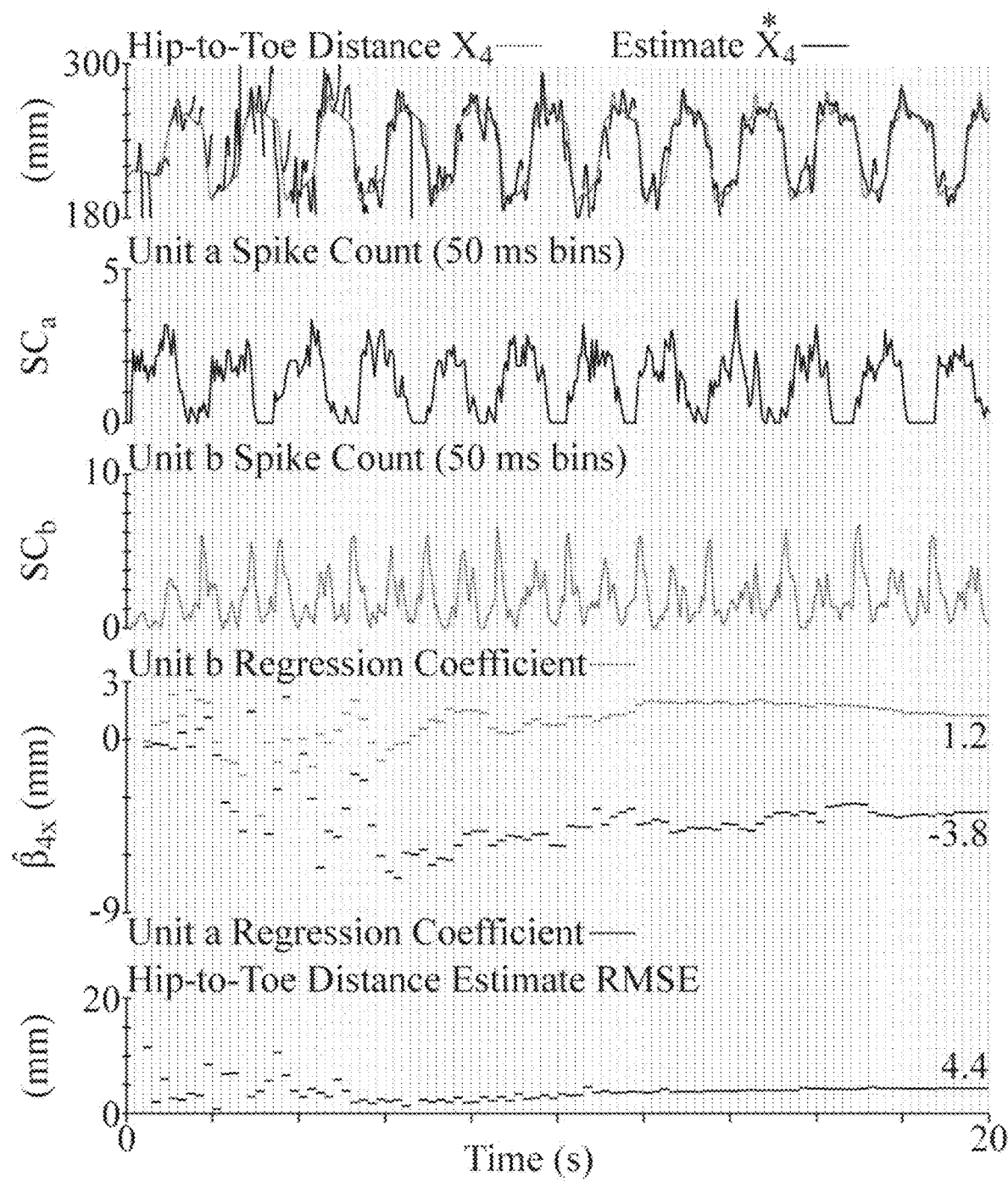
FIG. 10 is a set of graphs showing real-time regression model fitting (i.e. calibration) of a closed loop FES experiment.

Real-time decoding of lumbar DRG activity was performed in the experiments. In experiment I, 129 DRG units were used in the real-time model, which estimated the angular position of the hip, knee, and ankle joints ($X^*_{1,2,3}$). The estimated joint angles and measured segment lengths for the femur and shank were used to calculate an estimate for the toe position. At the end of the 61 s calibration period, which had 29 complete step cycles, the limb position estimate had an RMSE of 6.4 mm. In experiment K, 124 DRG units were used in the real-time model, which used polar coordinates ($X^*_{4,5}$) to estimate the toe position. In this experiment, a 73 s calibration period consisting of 28 complete limb step cycles led to a final limb position estimate RMSE of 4.8 mm. The first 20 s of the calibration period is recreated for cat K in FIG. 10. Each RMS error value is calculated from the start of the trial to the end of the previous interval using the current set of regression coefficients. The final RMS error for the angle ($X^*_5$) was 1.3 degrees.

Figure 11:
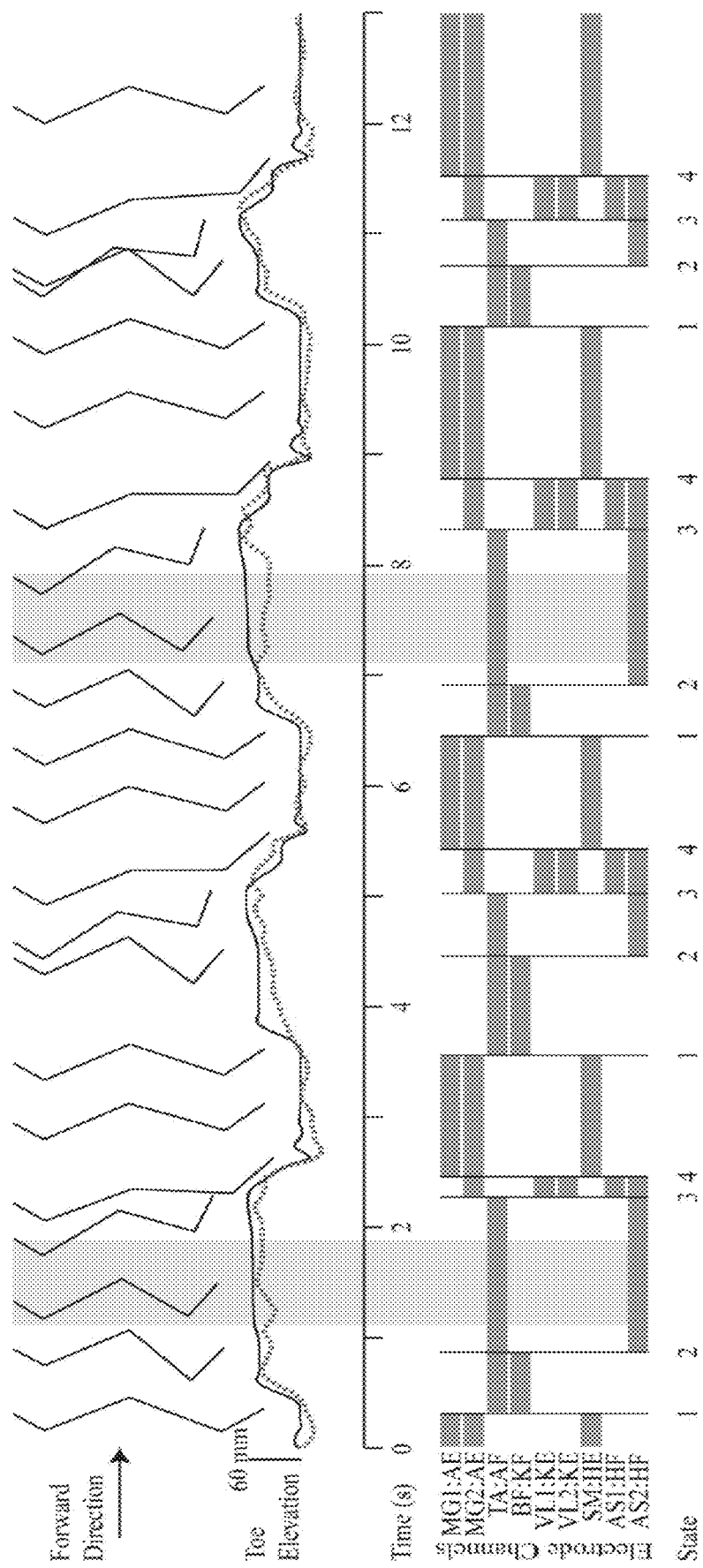
FIG. 11 is a graph showing closed loop FES control of the hind limb, indicated by the estimated limb position (dashed line) tracking the actual limb position (solid line), based on DRG recordings during normal and perturbed states (vertical shaded box). At the bottom, the different electrical stimulation patterns used to move the limb by a closed-loop controller are shown.

Closed-loop FES control of the left hind leg was obtained. Example step cycles and electrode combinations from cat K are shown in FIG. 11. In FIG. 11, the stick figures at top represent limb states at different time points, recreated from $X_{1-3}$. The actual ($X_4$; solid line) and estimated ($X^*_4$; dashed line) elevation of the toe are given. At the bottom, combinations of electrode channels used to move the limb and the controller state transitions are shown (A=ankle, K=Knee, H=Hip; E=extensor, F=flexor; muscle abbreviations defined above). During the first and third steps, forward movement of the limb was obstructed (shaded grey boxes) by the haptic robot attached to the foot, which otherwise provided only a virtual floor. During each step, the FES controller successfully moved the limb through the four states. Four distinct stimulation channel combinations were used for transitioning between the four states of the step cycle. As the foot was transitioned out of state 4, there were small oscillations resulting from contact with the haptic robot simulated floor.

In experiment I, a total of 74 complete FES-controlled stepping cycles were performed using DRG signals as feedback, of which 57 cycles were not impeded with a perturbation. Across six trials, 12.3±9.2 cycles were performed for 64.4±20.4 seconds per trial. Rest periods between closed-loop trials were 3.6±1.8 minutes. In cat K, a total of 94 complete FES-controlled stepping cycles were performed, of which 70 cycles were not impeded. Across seven trials, 13.4±6.2 cycles were performed for 77.6±8.2 seconds per trial. Rest periods between trials were 16.8±8.4 minutes. Partial stepping cycles, at the beginning of a trial when the limb moved to state 1 or at the end of a trial if recording was stopped before the limb returned to state 1 are not included in this summary.

A total of 20 manual perturbations were performed in cat I (1.01 s±0.47 s average duration) and 24 automated (i.e. robot-controlled) perturbations were performed in cat K (0.76 s±0.11 s average duration). After each perturbation, the controller correctly identified that the position of the limb had not yet reached the next state. This shows that the estimates of the limb state were not influenced by the stimulation itself and were based purely on sensory neural activity associated with the actual limb position. Once the perturbation ceased, the hind limb continued to advance toward the desired state and usually completed the step-cycle successfully. After eight of the perturbations, the controller first had to force the limb to re-enter the perturbed state before continuing due to movement that occurred during the perturbation. Two successful stepping cycles with perturbation are shown in FIG. 11.

This example illustrates that primary afferent recordings from lumbar DRG provide sufficient information for closed-loop control of the limb. All observed DRG units were used in the FES state controller. This approach allowed for a relatively quick setting of regression coefficients during the calibration period (FIG. 10), as non-relevant units with low regression coefficients were essentially ignored.

Neuroprosthesis users desire smoother gait during locomotion, improved energy efficiency and better balance. Integration of sensory feedback in closed-loop control of locomotion, as demonstrated here, will help address these objectives. Integrated sensory feedback provides users with a more natural control of locomotion by allowing FES controllers to react to perturbations and muscle fatigue. For FES recipients having surgery to receive implanted stimulating electrodes, DRG electrodes could be placed at the same time and connected to the implant electronics for easy integration, such as in a networked neuroprosthesis (see, e.g., Smith et al., Conference Proceedings of 2nd International IEEE EMBS Conference on Neural Engineering, 2005, pp. 454-457; and Peckham and Knutson, Annual Review of Biomedical Engineering, vol. 7, pp. 327-60, 2005, each of which is incorporated by reference herein in its entirety). For other individuals it may be possible to access the DRG with minimally invasive approaches, similar to insertion of Medtronic Interstim stimulation electrodes in the sacral foramen (see, e.g., Spinelli and Sievert, European Urology, vol. 54, no. 6, pp. 1287-96, December 2008, incorporated by reference herein in its entirety) or for insertion of the Spinal Modulation device near cervical DRG for pain management (Kim and Imran, U.S. Pat. No. 7,502,651, incorporated by reference herein in its entirety).

Example 5

Decoding of Limb-State from Sensory Neural Activity Recordings Made on Electrodes Closely Coupled to DRG Surface This example illustrates use of an embodiment of a disclosed method for monitoring limb-state or other physiological processes using sensory neural signals obtained from microelectrodes closely coupled to the surface of the DRG.

A laminectomy was performed in adult cats to expose the spinal cord and the sixth and seventh lumbar (L6 and L7) DRG. Leg motion was measured with a 3D motion capture system. The left hindpaw was fixed to an industrial robot that generated stereotyped movements of the limb. Non-penetrating microelectrode arrays were placed in direct contact with the DRG surface (epineurium). In this experiment, the electrode recording sites were 50 μm in diameter and were patterned on a flexible substrate that was placed in contact with the surface of the DRG. Neural activity signals were acquired using a multichannel neural signal recording system.

Neuronal action potential signals (i.e. spikes) from individual neurons were discriminated offline using commercial software. Units were classified as exhibiting single-unit activity if no more than 1% of the interspike-intervals (ISI) were less than 2.5 ms, otherwise units were identified as being multi-unit activity consisting of the superimposed signals of more than one single unit.

Multiple linear regression analysis was used to determine whether the activity of identified sensory neurons were modulated during hindlimb movement. Six kinematic parameters (angular position and velocity of the hip, knee and ankle) were used as the independent variables in the regression equation. Smoothed firing rates were calculated using a gaussian kernel with a 100 ms bin width. The coefficient of determination ($R^2$) was calculated from the regression between the smoothed firing rate and the kinematic variables and used as a metric to evaluate how much the firing rate of a given unit was modulated by hindlimb movement. In general, units with $R^2$ values less than 0.1 are described as not being modulated by movement of the hindlimb.

Figure 12A:
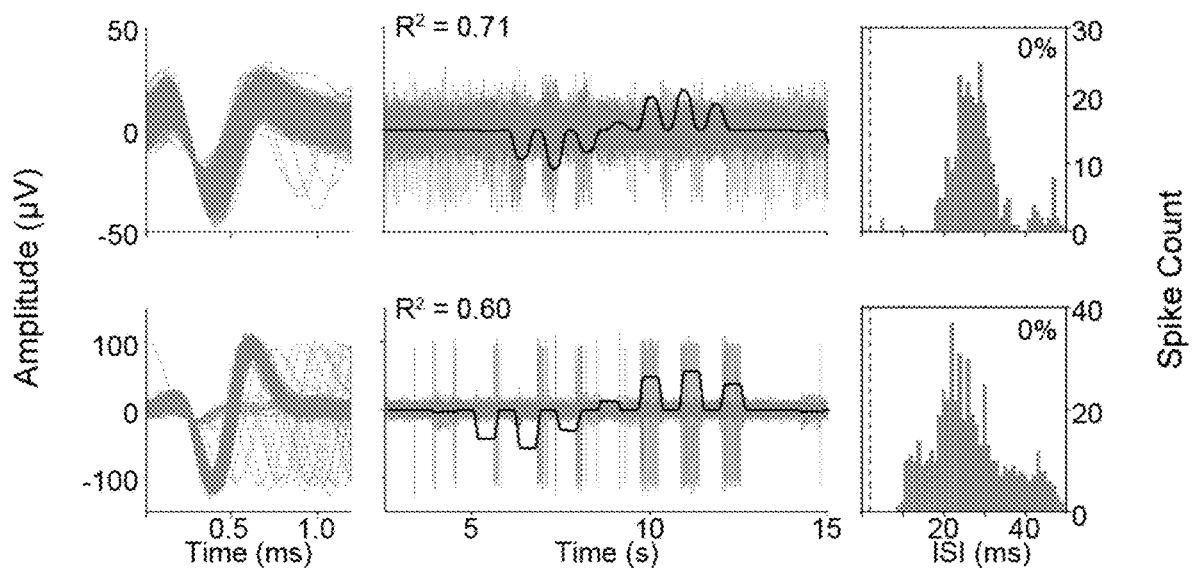
FIGS. 12A and 12B are a set of charts showing examples of neural recordings from the surface of the DRG using non-penetrating electrodes (FIG. 12A) and the regression modeling estimates of the knee and ankle joint angular positions based on the neural signal recordings (FIG. 12B).

Data collected in these experiments shows that modulated single unit neural activity can be recorded from the surface of DRG using non-penetrating electrodes. FIG. 12A shows two examples of single unit sensory neuron activity that were recorded from the DRG surface electrodes during passive movement of the hindlimb. The left column shows plots of the spike waveforms that were recorded and the right column shows the inter-spike interval (ISI) histograms. The 0% in each histogram indicates that no ISI was less than 2.5 ms for either neuron. In both of these example neurons, the regression analysis indicated significant modulation resulting from movement of the hindlimb (middle column of FIG. 12A). It is noteworthy that the amplitude and shape of the spike waveforms obtained with the DRG surface electrodes is similar to the quality of signals recorded with penetrating electrodes.

Figure 12B:
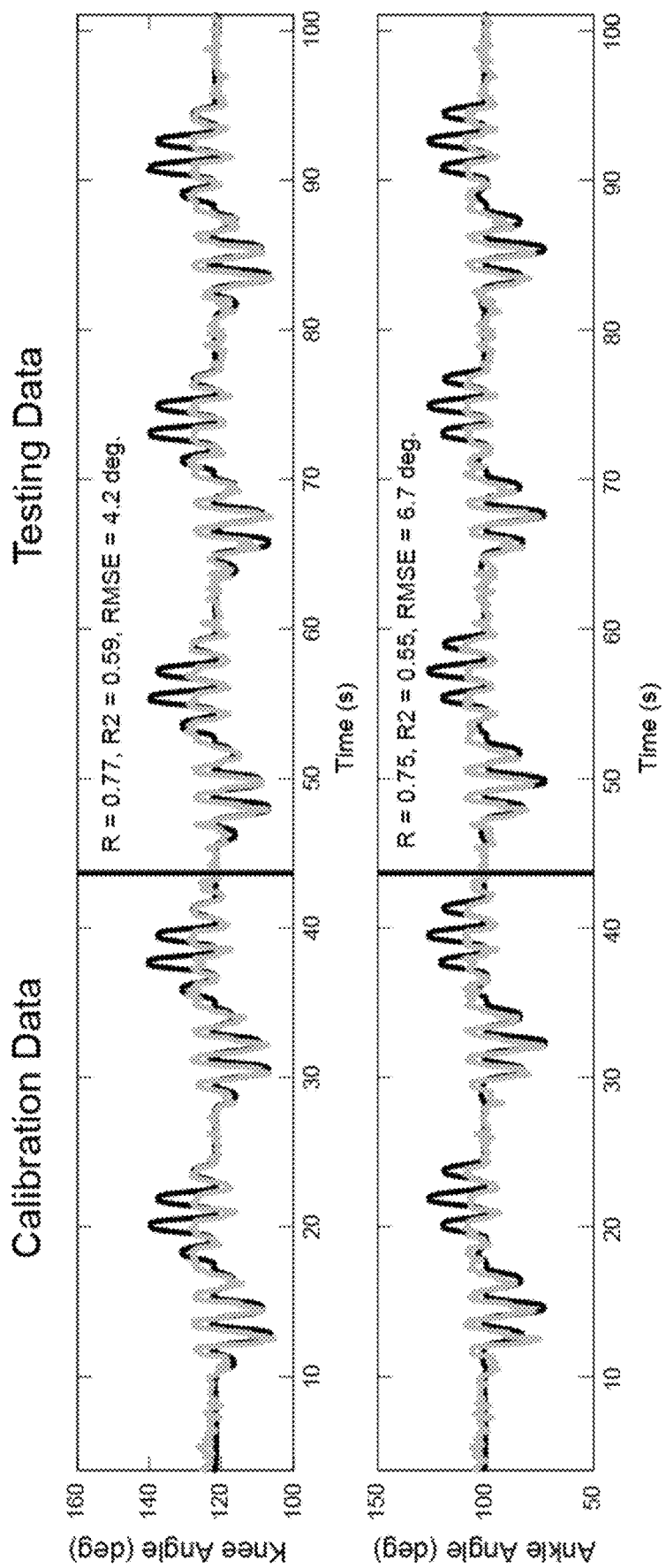

FIG. 12B demonstrates the ability to estimate the angular positions of the knee and ankle joints using neural recordings obtained with electrodes placed on the DRG surface. In these plots, the first 45 seconds of data were used to calibrate the regression model. The accuracy of the model was then tested in the remaining ~60 seconds of data. The black and gray traces in these plots represent the actual and estimated joint angles, respectively. The $R^2$ values and root-mean-squared errors (RMSE) are listed and indicate that the model estimates are very accurate.

The cell bodies of primary afferent neurons are located in the dorsal root ganglia (DRG) and many tend to be located near the perimeter of the DRG, which is surrounded by a relatively thin epineurium. This example demonstrates that non-penetrating surface electrodes can be used to record neural activity from individually isolated primary afferent cell bodies located in the DRG. It is surprising that the amplitude and isolation quality of these neural signals are comparable to those obtained with penetrating microelectrodes. This approach may improve the longevity of a neural interface at the DRG, because it avoids causing damage to the DRG as is produced during insertion of a penetrating electrode. A non-penetrating surface electrode might form the basis of a more effective neural interface at the DRG than more traditional penetrating microelectrode arrays.

It will be apparent that the precise details of the methods or apparatuses described may be varied or modified without departing from the spirit of the described embodiments. We claim all such modifications and variations that fall within the scope and spirit of the claims below.

We claim:

1. A method of inducing a physiological function of an organ or a tissue in a patient, comprising:
  contacting a dorsal root ganglion in the patient with a microarray, wherein the microarray comprises a plurality of individual electrodes each with a diameter of less than 100 μm, the method further comprising a calibration phase and an inducement phase, wherein:
  (A) the calibration phase comprises:
    stimulating sensory neuron activity with the individual electrodes to activate sensory neurons and/or a sensory reflex circuit that induces the physiological function of the organ or the tissue;
    measuring and/or monitoring activation of the physiological function of the organ or the tissue; and
    correlating the activation of the physiological function with the stimulated sensory neuron activity to identify individual electrodes that can activate the sensory neurons and/or the sensory reflex circuit that induces the physiological function; and
  (B) the inducement phase comprises:
    activating the sensory neurons and/or sensory reflex circuit by stimulating the sensory neurons with the identified individual electrodes to induce the physiological function of the organ or tissue in the patient.

2. The method of claim 1, wherein the microarray penetrates the dorsal root ganglion.

3. The method of claim 1, wherein the inducement phase is under user control.

4. The method of claim 1, wherein the organ comprises a bladder, urethra, and/or a urethral sphincter and the physiological function is bladder voiding.

5. The method of claim 1, wherein the organ comprises a rectum and/or an anal sphincter and the physiological function is bowel voiding.

6. The method of claim 1, wherein the organ comprises a bladder, urethra, and/or a urethral sphincter and the physiological function is continence.

7. The method of claim 1, wherein the organ comprises a rectum and/or an anal sphincter; and the physiological function is continence.

8. The method of claim 1, wherein the organ comprises a penis, and the physiological function is erectile function or ejaculation.

9. The method of claim 1, wherein the organ comprises a brain and the physiological function is sensation of a mechanical or an environmental stimulus.

10. The method of claim 1, wherein the organ comprises a brain and the physiological function is neuronal activity that masks or blocks sensation of pain.

11. The method of claim 1, wherein the tissue comprises a muscle and the physiological function is contraction or relaxation.

12. The method of claim 1, wherein the tissue comprises a muscle, the physiological function is limb movement, and the method comprises controlling limb movement in the patient, wherein:
  (A) the calibration phase comprises:
    stimulating a threshold sensory neuron activity with the individual electrodes to activate a sensory reflex circuit that induces the limb movement in the patient;
    measuring activation of the limb movement; and
    correlating activation of the limb movement with the stimulated threshold sensory neuron activity to identify individual electrodes that can activate the sensory reflex circuit that induces the limb movement; and (B) the inducement phase comprises:
  activating the sensory reflex circuit by stimulating the threshold sensory neuron activity with the identified individual electrodes to induce the limb movement in the patient.

13. The method of claim 1, wherein the plurality of individual electrodes comprises at least 5 electrodes with a surface area of less than 200,000 $\mu m^2$ each.

14. The method of claim 1, wherein the calibration phase and/or the inducement phase is performed using a computer.

15. The method of claim 1, wherein the organ or tissue comprises a bladder, urethra, and/or a urethral sphincter and the physiological function is bladder voiding, wherein
  (A) the calibration phase comprises:
    stimulating a threshold sensory neuron activity with the individual electrodes to activate a sensory reflex circuit that induces the bladder voiding in the patient;
    measuring activation of the bladder voiding; and
    correlating activation of the bladder voiding with the stimulated threshold sensory neuron activity to identify individual electrodes that can activate the sensory reflex circuit that induces the bladder voiding; and
  (B) the inducement phase comprises:
    activating the sensory reflex circuit by stimulating the threshold sensory neuron activity with the identified individual electrodes to induce the bladder voiding in the patient.

16. The method of claim 1, wherein the plurality of individual electrodes of the microarray contact a single dorsal root ganglion in the patient.

* * * * *

UNITED STATES PATENT AND TRADEMARK OFFICE
CERTIFICATE OF CORRECTION

| | | |
|---|---|---|
| PATENT NO. | : 11,433,241 B2 | Page 1 of 1 |
| APPLICATION NO. | : 15/462487 | |
| DATED | : September 6, 2022 | |
| INVENTOR(S) | : Weber et al. | |

It is certified that error appears in the above-identified patent and that said Letters Patent is hereby corrected as shown below:

In the Specification

Column 1, Lines 17-22, "This invention was made with government support under Grant Nos. EB007749 and NS056136 awarded by the National Institutes of Health and Grant No. W81XWH-07-1-0716 from the Telemedicine and Advanced Technology Research Center. The government has certain rights in the invention."
This should read --This invention was made with government support under Grant No. W81XWH-07-1-0716 awarded by the Defense Health Agency, Medical Research and Development Branch, and Grant Nos. EB007749 and NS056136 awarded by the National Institutes of Health. The government has certain rights in the invention.--

Signed and Sealed this
Second Day of September, 2025

Coke Morgan Stewart
*Acting Director of the United States Patent and Trademark Office*